US012417830B2

(12) United States Patent
Jacobs et al.

(10) Patent No.: US 12,417,830 B2
(45) Date of Patent: Sep. 16, 2025

(54) WEARABLE HEADS-UP DISPLAY ("HUD") FOR A PHARMACY WORKFLOW MANAGEMENT SYSTEM

(71) Applicants: BAXTER INTERNATIONAL INC., Deerfield, IL (US); BAXTER HEALTHCARE SA, Glattpark (CH)

(72) Inventors: Amanda Gloria Jacobs, Chicago, IL (US); Gregory Dean Kramer, St. Petersburg, FL (US); Jeffrey Robert Brittain, Charleston, SC (US); John Olson, Lake Zurich, IL (US); Christina Kappil, Crystal Lake, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 274 days.

(21) Appl. No.: 18/123,682

(22) Filed: Mar. 20, 2023

(65) Prior Publication Data

US 2023/0298721 A1 Sep. 21, 2023

Related U.S. Application Data

(60) Provisional application No. 63/321,488, filed on Mar. 18, 2022.

(51) Int. Cl.
*G16H 20/10* (2018.01)
*G09B 19/00* (2006.01)
(Continued)

(52) U.S. Cl.
CPC ........... *G16H 20/10* (2018.01); *G09B 19/003* (2013.01); *G10L 15/22* (2013.01); *G10L 15/26* (2013.01);
(Continued)

(58) Field of Classification Search
CPC ..................................................... G16H 20/10
See application file for complete search history.

(56) References Cited

U.S. PATENT DOCUMENTS 8,374,887 B1 2/2013 Alexander
2011/0267465 A1* 11/2011 Alexander et al. ...... H04N 7/18
(Continued)

OTHER PUBLICATIONS

International Preliminary Report on Patentability—PCT/US2023/064709 dated Feb. 19, 2024—22 pages.

*Primary Examiner* — James J Debrow
(74) *Attorney, Agent, or Firm* — K&L Gates LLP

(57) ABSTRACT

A wearable heads-up display ("HUD") for a pharmacy workflow management system is disclosed herein. An example HUD includes smart-glasses that are communicatively coupled to a client device. The smart-glasses include at least one camera and/or barcode scanner to record information needed for the verification of a medication dose during medication formulation preparation. The smart-glasses include at least one microphone to record voice commands. Further, the smart-glasses include at least one embedded display screen that shows sequential steps of a preparation protocol for guiding a pharmacy technician to prepare a medication dose. An application on the client device and/or the smart-glasses is configured to recognize and use voice commands to provide navigation for the embedded display screen. The voice commands may also be used to provide data entry for medication dose preparation verification. Gestures may be detected by the camera and translated by the application into navigation or data entry commands.

20 Claims, 17 Drawing Sheets

(51) Int. Cl.
　　　*G10L 15/22*　　　(2006.01)
　　　*G10L 15/26*　　　(2006.01)
　　　*H04N 23/69*　　　(2023.01)
　　　*H04N 23/90*　　　(2023.01)
　　　*H04R 1/02*　　　(2006.01)
　　　*G06F 3/16*　　　(2006.01)

(52) U.S. Cl.
　　　CPC ............. *H04N 23/69* (2023.01); *H04N 23/90* (2023.01); *H04R 1/028* (2013.01); *G06F 3/167* (2013.01); *G10L 2015/223* (2013.01); *H04R 2499/15* (2013.01)

(56) References Cited

U.S. PATENT DOCUMENTS

| | | | |
|---|---|---|---|
| 2017/0185716 A1* | 6/2017 | Rodriguez et al. | G06F 19/322 |
| 2017/0372034 A1 | 12/2017 | Tribble et al. | |
| 2021/0200193 A1* | 7/2021 | Friebe | G05B 19/41875 |

* cited by examiner

Preparing: 0.9% sodium chloride 50 mL, clindamycin 900 mg in 50 mL

0mL (Baxter Healthcare Corp)

| Required Ingredients | | |
|---|---|---|
| Ingredient | Scanned | Needed |
| 0.9% sodium | 0 mL | 50 mL |
| clindamycin | 900mg | 900 mg |

Prepare    clindam    [CANCEL PREP]    1 of 1    (Default)

[Enter/Scan] Enter Product Lot Number.
[Enter/Scan] Enter Product Expiration Date.
[Scan] Scan - any dose barcode

FIG. 7

```
6:12
Scan Ingredient                                          Baxter
Preparing: Cefazolin 1 g in 50 mL          [ CANCEL ]
Required Ingredients          Prepare Ingredients   SYRINGE
Ingredient   Scanned  Needed   Enter Product Lot Number.
Cefazolin       0       1g     0679
                               Enter Mfg Exp Date
                               10/3/2023
                               Scan diluent for reconstitution.
                               Allowed Reconstitution Diluents
                               r reconstitution           Acquire
```
1600

FIG. 19

```
6:15
Partial volume scanned. Still need: 76 ml             Baxter
Product                                       Contributing
Sterile Water 20mL (Hospira)                     20ml
                        14
            [ ENTER DILUENT LOT ]  [ ENTER DILUENT MFG EXP ]

OK                   SCAN    CLOSE
```
2000

FIG. 20

WEARABLE HEADS-UP DISPLAY ("HUD") FOR A PHARMACY WORKFLOW MANAGEMENT SYSTEM

PRIORITY CLAIM

This application claims priority to and the benefit as a non-provisional application of U.S. Provisional Patent Application No. 63/321,488, filed on Mar. 18, 2022, the entire contents of which are hereby incorporated by reference and relied upon.

BACKGROUND

In hospitals, patients are administered medication in the form of pills or prepared medication formulations. Every year in the United States, over 160 million doses of medication formulations are prepared in hospital pharmacies. The medication formulations may be in the form of solutions for intravenous ("IV") administration, oral administration, subcutaneous injections, or intramuscular injections, for example. The solutions may include drugs or nutrients for parenteral nutrition. The solutions are typically administered by an infusion pump, gravity feed, or a syringe.

Of these 160 million annual doses, it is estimated that unfortunately 4% to 7% are prepared or otherwise compounded in error. These errors and the waste associated with them account for at least 3% of medication costs. Pharmacy Workflow Management Software ("PWMS"), such as the known PWMS included with a pharmacy automation system 100 shown in FIG. 1, is configured to prevent or catch these medication preparation errors. Recent studies have shown that 14× more medication errors reach patients for medications that are prepared manually compared to medications prepared through the guidance and verification provided by PWMS.

The known pharmacy automation system 100 includes a preparation station 102 containing a camera and a weight scale or balance 103. The system 100 also includes a barcode scanner 104. As shown in FIG. 1, the preparation station 102 and the barcode scanner 104 are located in a direct compounding area within a primary engineering control laminar flow hood or a biological safety cabinet ("BSC"). Both the preparation station 102 and the barcode scanner 104 are communicatively coupled to a computer 106, which is located outside of the direct compounding area but within the pharmacy clean room environment. To prepare a medication formulation, a technician uses the computer 106 to select a prescribed medication dose order for a patient. Selection of the medication dose order causes the PWMS on the computer 106 to display a sequence of steps for preparing a dose to fulfill the dose order. The system 100 further includes a printer 108 for preparing labels that are affixed to medication containers that house prepared medication formulations. Alternatively, the printer 108 may be used for preparing labels that are affixed to drug vials or used for intermediate steps of a complex drug preparation process.

To provide verification that the dose was prepared according to the sequence of steps, the PWMS prompts the technician to perform certain actions. The actions may include scanning ingredients and medication containers with the barcode scanner 104 to verify use of the correct ingredients, weighing ingredients or medication containers with the scale or balance 103 of the preparation station 102, and capturing images of certain preparation steps with the camera of the preparation station 102. Barcode data, weight data, images, and technician inputs are recorded by the PWMS of the computer 106 and stored to a verification record. A pharmacist locally or remotely reviews the verification record to confirm the medication formulation was prepared correctly. After verification, the medication container is released for administration to a patient.

The pharmacy clean room environment is usually an ISO Class 5 or higher environment for compounding sterile medication doses. As a technician progresses through the sequence of steps, the technician has to routinely interact with a touchscreen of the computer 106 to receive instruction prompts and enter dose preparation verification information. For example, a technician may use the touchscreen to select a dose from a dose order queue, enter a lot and expiration date of an ingredient after a scan, or review a recorded image. Since the touchscreen is outside of the direct compounding area, the technician has to decontaminate their hands (e.g., spray gloved hands with a sterile isopropyl alcohol) every time the touchscreen is touched. Each decontamination can take up to 30 seconds. For a single dose preparation, a technician may interact with the touchscreen four to twenty times, which can add many minutes of time to prepare every medication formulation. As one can appreciate, this extra decontamination time is inefficient and may lead to some technicians skipping decontamination and risking contamination or preparation errors.

SUMMARY

The example system, apparatus, and methods disclosed herein are configured to provide medication formulation preparation using a heads-up display ("HUD") system. The HUD system includes smart-glasses that have at least one camera, a barcode scanner, a microphone, and an embedded display screen provided adjacent to one of the lenses. Instead of interacting with the computer 106 of FIG. 1, the embedded display provides the steps for preparing the medication formulation. Further, the microphone is configured to record voice commands and/or the camera is configured to record images of technician gestures to provide hands-free interaction.

The HUD system disclosed herein also includes a client device that is communicatively coupled to the smart-glasses via a wired or wireless connection. An application on the client device is configured to manage a medication dose preparation sequence and communicate with the smart-glasses to display preparation instructions on the embedded display screen. The application is also configured to process voice commands to perform certain operations or provide data entry. The application is further configured to process images from the camera to interpret gestures for performing certain operations, identify/read barcodes, and/or store images for later pharmacist verification.

The example HUD system disclosed herein is configured to increase pharmacy efficiency during medication dose preparation by reducing a need for a technician to remove their hands from the sterile direct compounding area. For example, instead of having to contact a touchscreen, the HUD system provides voice and/or gesture data entry and step progression. Removal of a touchscreen also empowers technicians to focus on drug preparation tasks, thereby minimizing distractions and reducing the risk of dose preparation errors by presenting instructions for dose preparation to the technician without requiring them to look away from their field of view. The example HUD system also improves technician productivity by using voice or gesture activated work instruction commands, thereby decreasing the need for repetitive breaches of the sterile direct compounding area.

The HUD system can save many minutes of dose preparation time. Over the course of an eight-hour shift, this can add up to hours of saved time for a single technician.

The example HUD system is also configured to enable remote communication between the direct compounding area and a remote pharmacy verification system. A technician may place a live call to a pharmacist to ask for assistance, obtain an answer to a question, or otherwise receive pharmacy verification without having to leave the direct compounding area, thereby helping to reduce dose preparation time and increase efficiency. The HUD system also reduces ambiguity of doses that are rejected or sent for re-work (during pharmacy verification) by enabling 2-way communication between the direct compounding area and a verifying pharmacist. The HUD system accordingly enables live or recorded remote pharmacy drug verification without compromising direct compounding area sterility.

In light of the disclosure herein and without limiting the disclosure in any way, in a first aspect of the present disclosure, which may be combined with any other aspect listed herein unless specified otherwise, a heads-up display ("HUD") system includes an eyewear device comprising a frame including a right lens, a left lens, a bridge connecting the right lens and the left lens, a first arm connected to the right lens, and a second arm connected to the left lens, a camera positioned on or integrated with the frame, a microphone and speaker connected to or integrated with the first arm or the second arm, and a display module including a screen that is positioned in front of or behind the right lens or the left lens with respect to a viewpoint of a wearer. The system also includes a client device communicatively coupled to the eyewear device. The client device includes a processor and a memory device storing instructions defining an application. Execution of the instructions causes the processor of the client device to cause the application to communicatively couple to a pharmacy server storing a plurality of dose orders for medication doses ordered for preparation and cause the display module of the eyewear device to display a user interface that includes at least a portion of the plurality of dose orders. Execution of the instructions also causes the processor of the client device to receive an input via the microphone or the camera indicative of a dose order for selection, receive a dose order file from the pharmacy server, the dose order file corresponding to the selected dose order, and receive or retrieve a preparation protocol based on a medication type of the dose order file. The preparation protocol includes a sequence of steps for preparing a medication dose for the selected dose order. Each step in the sequence of steps is associated with graphical step instructions for the wearer. At least one of the steps of the sequence of steps requires a digital image to be recorded. For each step of the preparation protocol, execution of the instructions causes the processor of the client device to display corresponding graphical step instructions on the screen of the eyewear device. When a step of the preparation protocol requires the recording of a digital image, execution of the instructions causes the processor of the client device to activate the camera for recording a digital image. When a step of the preparation protocol requires user entry of verification information, execution of the instructions causes the processor of the client device to (i) display, in conjunction with graphical step instructions of the step, options for voice entry via the microphone or digital image entry via the camera, and (ii) automatically progress to a next step of the preparation protocol after the verification information is received. Execution of the instructions further causes the processor of the client device to store to a verification file, an indication of a completion progress of the preparation protocol, recorded digital images, and the verification information.

In accordance with a second aspect of the present disclosure, which may be used in combination with any other aspect listed herein unless stated otherwise, the graphical step instructions for each step are displayed adjacent to a graphical indication of required ingredients that specifies a quantity of each ingredient needed and a quantity of each ingredient already obtained.

In accordance with a third aspect of the present disclosure, which may be used in combination with any other aspect listed herein unless stated otherwise, the application is configured to authenticate a wearer with the pharmacy server before having access to the plurality of dose orders, and the plurality of dose orders are selected by the server among all received dose orders based on the authentication of the wearer.

In accordance with a fourth aspect of the present disclosure, which may be used in combination with any other aspect listed herein unless stated otherwise, the at least one step of the sequence of steps requires the recording of the digital image of at least one of a label or a barcode of an ingredient container, a preparation container, a display of a weight scale or balance, or an administration container.

In accordance with a fifth aspect of the present disclosure, which may be used in combination with any other aspect listed herein unless stated otherwise, the camera is a first camera module that is located on the bridge, the eyewear device including a second camera module located on the left arm or the right arm.

In accordance with a sixth aspect of the present disclosure, which may be used in combination with any other aspect listed herein unless stated otherwise, the first camera module includes a high-resolution camera with at least five mega-pixels and the second camera module includes an optical zoom, a barcode scanner, and a laser pointer.

In accordance with a seventh aspect of the present disclosure, which may be used in combination with any other aspect listed herein unless stated otherwise, a touchpad is included with the second camera module or a housing of the microphone and speaker.

In accordance with an eighth aspect of the present disclosure, which may be used in combination with any other aspect listed herein unless stated otherwise, the processor of the client device in conjunction with the second camera module causes the second camera module to zoom and crop a digital image around a detected label or a barcode.

In accordance with a ninth aspect of the present disclosure, which may be used in combination with any other aspect listed herein unless stated otherwise, the graphical step instructions are first graphical step instructions for display at the eyewear device, the preparation protocol including second graphical step instructions that are configured for display on the client device, the second graphical step instructions including additional preparation content compared to the first graphical step instructions.

In accordance with a tenth aspect of the present disclosure, which may be used in combination with any other aspect listed herein unless stated otherwise, the processor is configured to receive, from the microphone of the eyewear device, an audio signal, convert the audio signal into text, determine the text corresponds to a voice command to start a video call with a pharmacist, use a video conference feature of the client device to connect to a device of the pharmacist, and activate the camera to transmit recorded video to the device of the pharmacist during the video conference.

In accordance with an eleventh aspect of the present disclosure, which may be used in combination with any other aspect listed herein unless stated otherwise, a heads-up display ("HUD") system includes an eyewear device comprising a frame including a right lens, a left lens, a bridge connecting the right lens and the left lens, a first arm connected to the right lens, and a second arm connected to the left lens, a barcode scanner positioned on or integrated with the frame, a microphone and speaker connected to or integrated with the first arm or the second arm, and a display module including a screen that is positioned in front of or behind the right lens or the left lens with respect to a viewpoint of a wearer. The system also includes a client device communicatively coupled to the eyewear device. The client device includes a processor and a memory device storing instructions defining an application. Execution of the instructions cause the processor of the client device to cause the application to communicatively couple to a pharmacy server storing a plurality of dose orders for medication doses ordered for preparation and cause the display module of the eyewear device to display a user interface that includes at least a portion of the plurality of dose orders. Execution of the instructions also cause the processor of the client device to receive an input via the microphone indicative of a dose order for selection, receive a dose order file from the pharmacy server, the dose order file corresponding to the selected dose order, and receive or retrieve a preparation protocol based on a medication type of the dose order file, the preparation protocol including a sequence of steps for preparing a medication dose for the selected dose order. Each step in the sequence of steps is associated with graphical step instructions for the wearer. At least one of the steps of the sequence of steps requires a barcode of an ingredient container for the medication dose to be recorded. Execution of the instructions further cause the processor of the client device to display, for each step of the preparation protocol, corresponding graphical step instructions on the screen of the eyewear device. When a step of the preparation protocol requires the recording of a barcode, the processor activates the barcode scanner. When a step of the preparation protocol requires user entry of verification information, the processor (i) displays, in conjunction with graphical step instructions of the step, a text box for voice entry via the microphone, and (ii) automatically progresses to a next step of the preparation protocol after the verification information is received. Additionally, execution of the instructions cause the processor of the client device to store to a verification file, an indication of a completion progress of the preparation protocol, data from scanned barcodes, and the verification information.

In accordance with a twelfth aspect of the present disclosure, which may be used in combination with any other aspect listed herein unless stated otherwise, when the step of the preparation protocol requires user entry of the verification information, the processor is configured to display, in conjunction with a user interface of the step, options for voice entry via the microphone or barcode scanning using the barcode scanner.

In accordance with a thirteenth aspect of the present disclosure, which may be used in combination with any other aspect listed herein unless stated otherwise, the processor is configured to compare verification information to verification limits specified in the preparation protocol, when at least some of the verification information is outside of the respective verification limits, cause an error message to be displayed by the display screen of the eyewear device, and when the verification information is within the respective verification limits, store the verification information to the verification file.

In accordance with a fourteenth aspect of the present disclosure, which may be used in combination with any other aspect listed herein unless stated otherwise, the comparison to the verification limits is performed during each step, and wherein the processor is configured to prevent graphical step instructions for a next step from being displayed at the display screen of the eyewear device until the verification information is within the respective verification limits.

In accordance with a fifteenth aspect of the present disclosure, which may be used in combination with any other aspect listed herein unless stated otherwise, the processor is configured to receive, from the microphone of the eyewear device, an audio signal, convert the audio signal into text, determine the text corresponds to a voice command to call a pharmacist, and use a call feature of the client device to connect to a device of the pharmacist.

In accordance with a sixteenth aspect of the present disclosure, which may be used in combination with any other aspect listed herein unless stated otherwise, the eyewear device further includes at least one camera module having a camera to record at least one of digital images or video for at least some of the verification information.

In a seventeenth aspect of the present disclosure, any of the structure, functionality, and alternatives disclosed in connection with any one or more of FIGS. 2 to 22 may be combined with any other structure, functionality, and alternatives disclosed in connection with any other one or more of FIGS. 2 to 22.

In light of the present disclosure and the above aspects, it is therefore an advantage of the present disclosure to provide an HUD system that enables an operator to prepare medication doses without having to breach a sterile direct compounding area.

It is another advantage of the present disclosure to use an HUD system to seamlessly record verification information related to medication dose preparation.

It is yet another advantage of the present disclosure to provide an HUD system that enables a technician to communicate with a remote pharmacist during medication dose preparation without having to breach the sterile direct compounding area.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

FIG. 7 is a diagram of a user interface that is displayed by an application on the display screen of the eyewear device, according to an example embodiment of the present disclosure.

FIGS. 16 to 22 are diagrams of example graphical user interfaces corresponding to activated modalities of the eyewear device of FIGS. 2 and 3 for preparing a medication dose, according to example embodiments of the present disclosure.

DETAILED DESCRIPTION

A wearable heads-up display ("HUD") system for a pharmacy workflow management system or PWMS is disclosed. The HUD system includes smart-glasses that are communicatively coupled to a client device. The smart-glasses include at least one camera and/or barcode scanner to record information needed for the verification of a medication dose during medication formulation preparation. The smart-glasses include at least one microphone to record voice commands. Further, the smart-glasses include at least one embedded display screen that shows sequential steps of a preparation protocol for guiding a pharmacy technician to prepare a medication dose. An application on the client device and/or the smart-glasses is configured to recognize and use voice commands to provide navigation for the embedded display screen. The voice commands may also be used to provide data entry for medication dose preparation verification. Additionally or alternatively, gestures may be detected by the camera and translated by the application into navigation or data entry commands.

Figure 1:
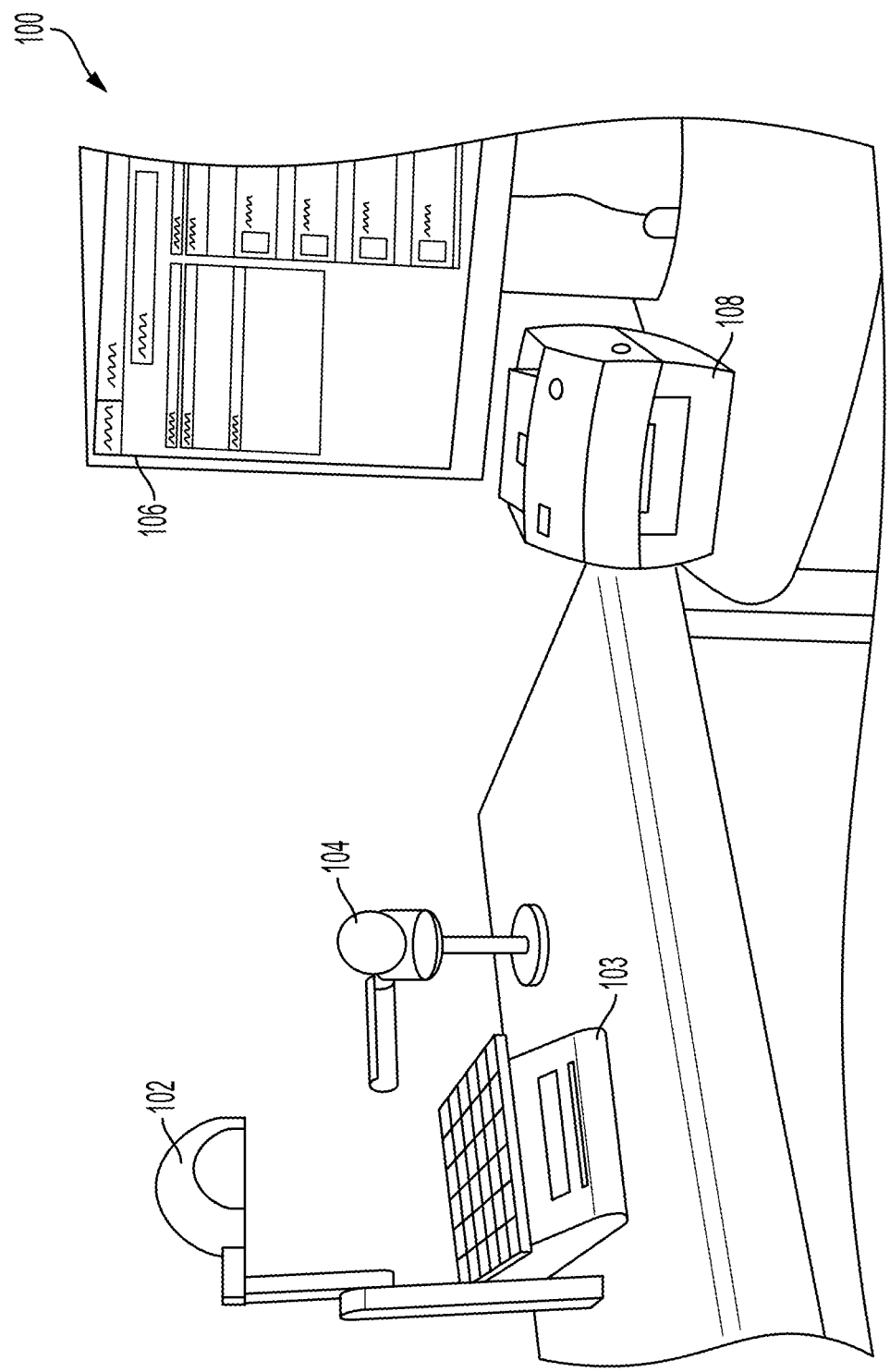
FIG. 1 is a diagram of a known pharmacy automation system.

Compared to the known pharmacy automation system 100 of FIG. 1, the HUD system disclosed herein reduces the amount of equipment within a laminar flow hood or BSC while not interfering with ISO Class 5 environment compliance. The HUD system also reduces potential contamination and non-compliance with sterility protocols by ensuring a technician does not have to contact a non-sterile touchscreen or otherwise leave a laminar flow hood or BSC during preparation of a medication dose. Further, the on board camera of the smart-glasses improves visibility of the preparation process since images are recorded from a point of view of the technician rather than the camera in the preparation station 102. Further, the use of the on board microphone and speakers (or speakers on the client device) enable two-way communication with a pharmacist during the preparation process without causing the technician to breach sterility of the laminar flow hood or BSC.

Reference is made herein to an HUD system that provides for the preparation of medication doses. As disclosed herein, a medication dose includes a fluid or a solid (e.g., a medication formulation) that is prepared from one or more ingredients. The fluid may include a solution for intravenous administration via an infusion pump, a syringe pump, or a gravity infusion. Alternatively, the fluid may include a solution for administration via a needle/syringe. In yet other embodiments, the medication dose may include a pill or powder that is administered orally, topically, or rectally to a patient.

As disclosed herein, the HUD system is configured to provide an interactive interface that records verification information to ensure an operator performed a certain process as instructed or specified by a sequence of dose protocol steps/instructions. Reference is also made herein to the use of the HUD system for medication dose preparation in a pharmacy system. However, it should be appreciated that the HUD system may be used for other applications. For example, the HUD system may be used to document the performance of a surgical procedure or medical procedure. In other instances, the HUD system may be used to provide step-by-step instructions for performing a medical procedure, where assistance may be remotely provided by a more experienced physician/surgeon. As such, the HUD system may be used by first-responders. In other embodiments, the HUD system may be used in manufacturing applications for guiding operators and enable quick calls for assistance from a remote supervisor. As one can appreciate, the number of uses for the HUD system is virtually limitless.

HUD System Embodiment

Figure 2:
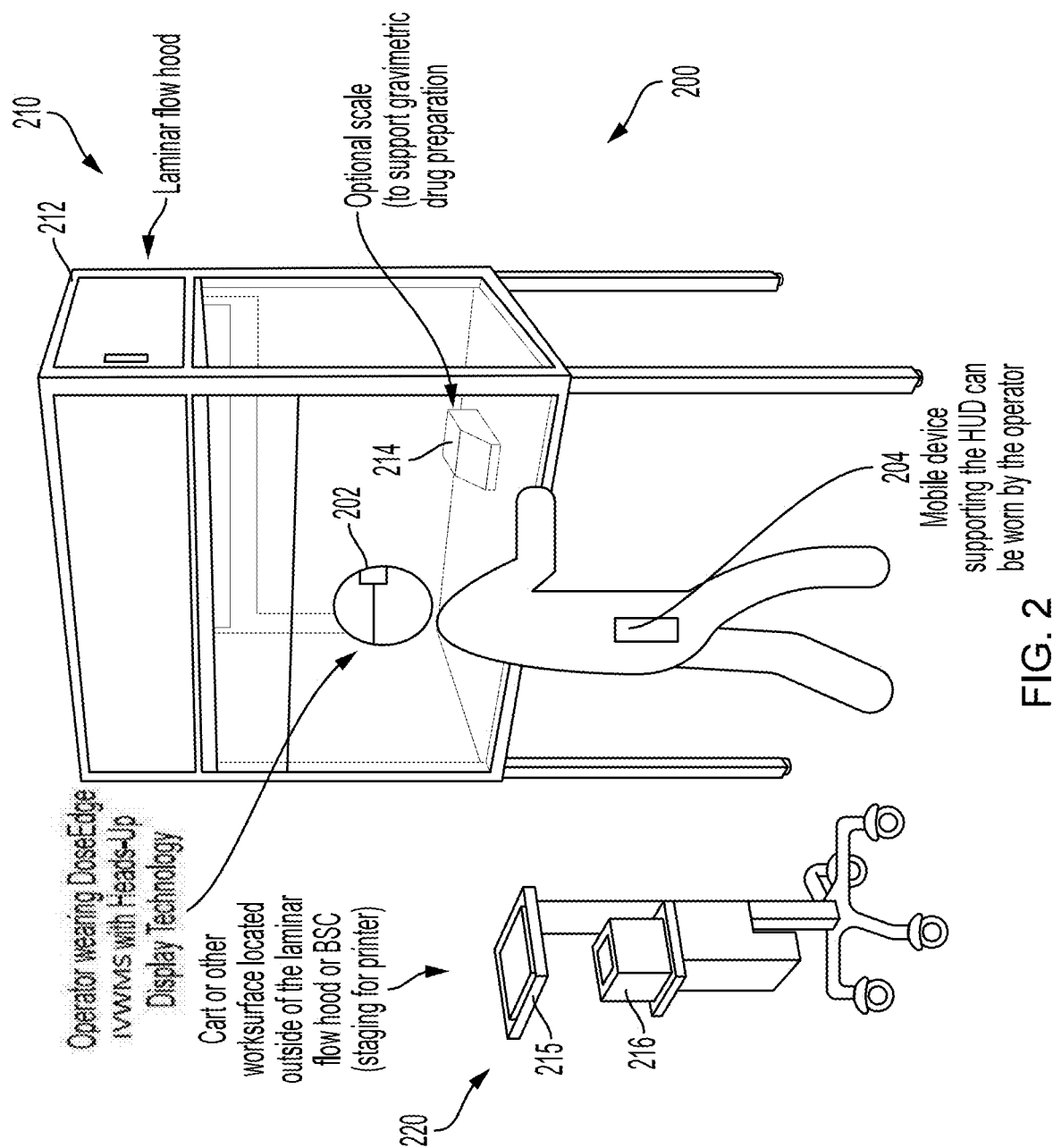
FIG. 2 is a diagram of an HUD system including an eyewear device and a client device, according to an example embodiment of the present disclosure.

Referring now to the drawings, FIG. 2 is a diagram of an HUD system 200, according to an example embodiment of the present disclosure. The HUD system 200 includes an eyewear device 202 (e.g., smart-eyewear) that is worn by a pharmacy technician (e.g., a wearer or a user). The HUD system 200 also includes a client device 204 that is communicatively coupled to the eyewear device 202. As discussed below in connection with FIG. 3, the client device 204 determines content for display by the eyewear device 202 and processes inputs received from the eyewear device 202.

The example HUD system 200 is for use within a dose preparation area 210, which may include a primary engineering control laminar flow hood or BSC 212 and a weight scale and/or balance 214 (optional). The laminar flow hood or BSC 212 provides a workspace with required air quality for a pharmacy technician to prepare medication doses, as specified by dose orders. The laminar flow hood or BSC 212 may be configured to conform to an ISO Class 5 or higher environment for cleanliness or sterility.

The medication doses prepared in the laminar flow hood or BSC 212 are generally patient-specific such that a single dose is prepared at a time. However, some medication doses may not be patient-specific and may instead be prepared in larger batches. As discussed in more detail below, the pharmacy technician uses the laminar flow hood or BSC 212 to compound one or more ingredients such as active ingredients and diluents to prepare a medication dose for administration.

FIG. 2 also shows an area 220 next to the dose preparation area 210. The area 220 may include a cart 215 with an additional workspace surface. In some embodiments, the cart 215 may be used to hold the client device 204 when the client device 204 is not worn by the technician. The cart 215 may also include a printer 216 that is configured to print labels. A label may be printed, for example, after completion and/or verification of a medication dose. The label is affixed to an administration container, such as an IV bag or a syringe for appropriate tracking within a medical facility. In some embodiments, labels may be printed for intermediate steps of a complex preparation process.

Figure 3:
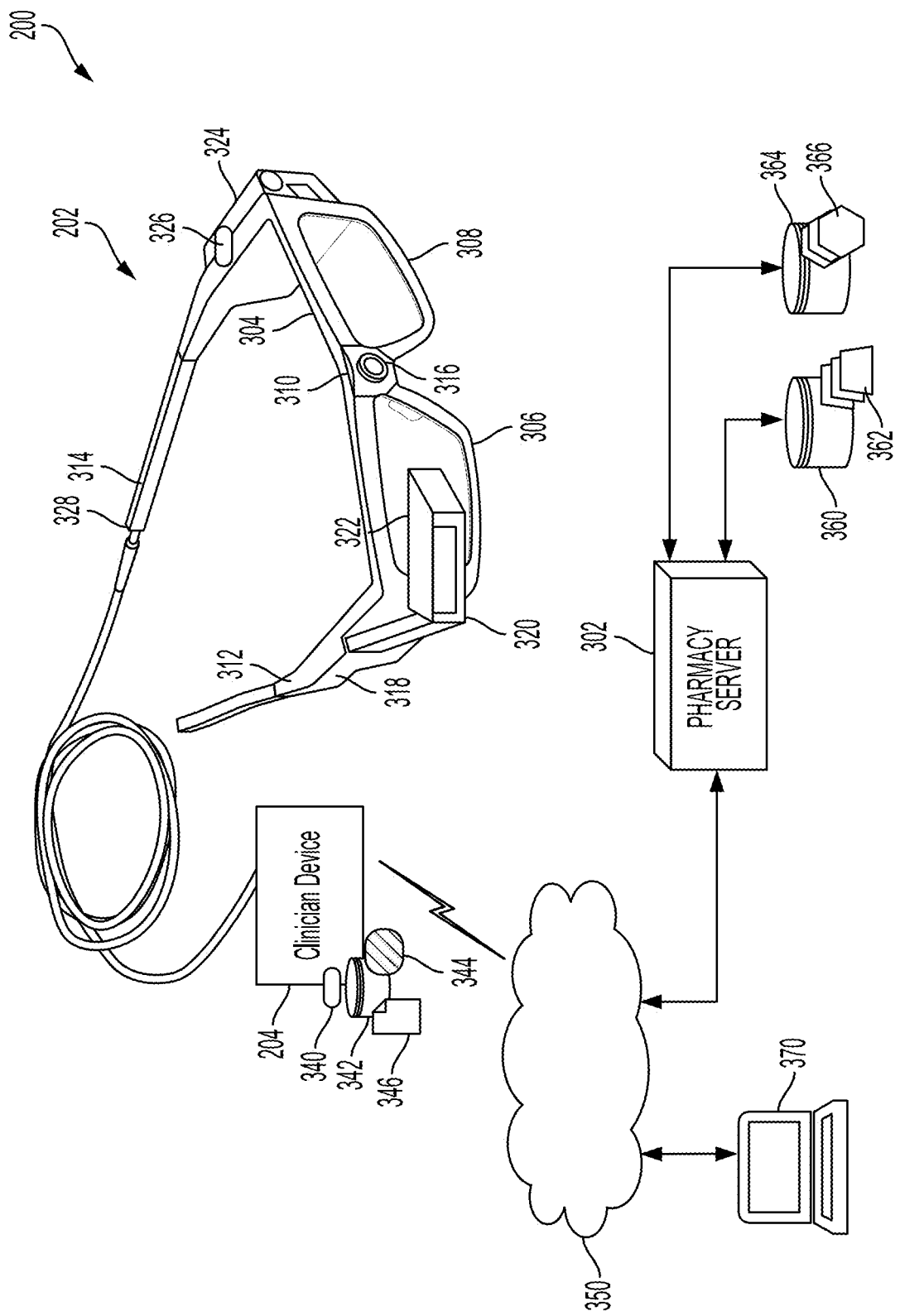
FIG. 3 is a diagram of the HUD system including the eyewear device and the clinician device of FIG. 2 in addition to a pharmacy server, according to an example embodiment of the present disclosure.

FIG. 3 is a diagram of the HUD system 200 including the eyewear device 202 and the clinician device 204 of FIG. 2 in addition to a pharmacy server 302, according to an example embodiment of the present disclosure. In some embodiments, the eyewear device 202 may include the IRISTICK H1™, IRISTICK.G2™, or IRISTICK.G2 PRO™ manufactured by Iristick NV®. In other embodiments, the eyewear device 202 may include other types or models of smart-glasses.

In the illustrated embodiment, the eyewear device 202 is a pair of glasses worn by a pharmacy technician. The eyewear device 202 includes a frame 304 that comprises a right lens 306 and a left lens 308. The lenses 306 and 308 may include a transparent plastic or glass. In some embodiments, the lenses 306 and 308 are polarized and/or configured for vision correction of a wearer. The frame 304 also includes a bridge 310 that connects the lenses 306 and 308.

The frame 304 also includes a first arm 312 that is connected to the right lens 306 and a second arm 314 that is connected to the left lens 308. The arms 312 and 314 are configured to secure the eyewear device 202 over a wearer's ears and temple area. In some embodiments, the arms 312 and 314 each include a joint to enable at least a portion of the arms to rotate or fold inward for portability.

The frame 304 further includes a first camera module 316 that is located at the bridge 310. The first camera module 316 includes a camera that is positioned or integrated with the frame 304. The camera of the first camera module 316 may be a high resolution camera with at least five megapixels, preferably around 15 or 16 megapixels. The camera is configured to have a field of view between 90 to 150 degrees to enable the recording of images in substantially the same field of view as a wearer. The first camera module 316 is configured to record still images or video at, for example, 1080p (full high-definition) at 30 to 60 frames per second.

The eyewear device 202 of FIG. 3 also includes a microphone and speaker module 318 that is integrated, connected to, or included within the first arm 312. In other examples, the microphone and speaker module 318 may be included with the frame 304 or the second arm 314. The microphone may include a single microphone or dual microphones with beamforming optimization corresponding to a wearer's mouth area. The speaker may include any speaker and is located on the first arm 312 for placement adjacent to a wearer's right ear. The microphone and speaker module 318 may also include a jack or port for an earpiece connection. Further, an exterior surface of the microphone and speaker module 318 may include a touchpad configured to receive inputs from a wearer. The inputs may be used to move a pointer shown on a display screen.

The eyewear device 202 also includes an embedded display module 320 that is connected to the first arm 312 via a hinge. In other examples, the display module 320 is connected to the frame 304. The display module 320 includes an L-shaped arm that provides 3-axes of adjustment with respect to the first arm 312. The L-shaped arm is configured to pivot to enable the display module 320 to be removed from a wearer's view. The L-shaped arm is also configured to place a display screen 322 adjacent to the right lens 306. While the display screen 322 is shown positioned behind the right lens 306 with respect to a viewpoint of a wearer, in other examples, the display screen 322 may be positioned in front of the right lens 306. Further, in other embodiments, the display module 320 may be connected to the second arm 314. Alternatively, the display screen 322 may be integrated with the right lens 306 and/or the left lens 308 such that the L-shaped arm is not needed. The display screen 322 may have a resolution of 426×240 wide quarter VGA ("WQVGA"), for example. Further, the display screen 322 is configured to display static images, video, and/or one or more computerized graphical user interfaces.

The eyewear device 202, in some embodiments, may also include a second camera module 324 that is connected to or integrated with the second arm 314. The second camera module 324 includes a camera that has a lower resolution than the camera of the first camera module 316. For instance, the camera of the second camera module 324 may have a resolution that is less than five megapixels. The camera of the second camera module 324 may have a field of view that is between 10 and 50 degrees. The camera may record single images or video at 720p at 30 frames per second, for example. The camera may also include an optical zoom that is between 2× and 10×, preferably 6×. Further, the camera of the second camera module 324 may include a liquid lens for relatively quick autofocus. The second camera module 324 may include a light emitting diode ("LED") to provide illumination for the camera or a dose preparation area.

In some embodiments, the second camera module 324 includes a barcode scanner for scanning barcodes provided on ingredient containers or labels applied to administration containers (e.g., an IV bag, syringe, etc.). The second camera module 324 may also include a class 1 laser that is configured to project a beam to indicate a center of a field of view of the barcode scanner and/or the camera (e.g., a laser pointer). The laser enables a wearer to orientate their head to ensure a barcode or container is within a field of view of the camera of the second camera module 324 and/or the camera of the first camera module 316.

The eyewear device 202 of FIG. 3 may further include a movement sensor. For example, a 9-axis sensor (accelerometer, gyroscope, compass, etc.) may be included within the second camera module 324, the first camera module 316, or another section of the frame 304. The eyewear device 202 may further include one or more batteries to provide local power. Moreover, a touchpad may be provided on an exterior surface of the second camera module 324.

In some additional embodiments, the eyewear device 202 may include a processor 326 that is communicatively coupled to the first camera module 316, the display screen 322, the microphone and speaker module 318, and/or the second camera module 324. The processor 326 is configured to execute instructions that enable the eyewear device 202 perform the operations described herein. The processor 326 may include a transceiver for wired or wireless communication with the client device 204. FIG. 3 shows a wired connection with the client device 204 via an I/O port 328. In this embodiment, the wired connection may also provide power from the client device 204 in addition to data communication. In alternative embodiments, the transceiver of the processor 326 may be configured to communicate with the client device 204 via a Bluetooth®, Zigbee®, or Wi-Fi protocol.

The client device 204 of FIG. 3 may include a smartphone, a tablet computer, a laptop computer, a desktop computer, a workstation, etc. In instances where the client device 204 is a smartphone, the client device 204 may be worn by a technician, as shown in FIG. 2. In instances where the client device 204 is a tablet computer, desktop computer, etc., the client device 204 may be placed on the cart 215.

The client device 204 includes a processor 340 and a memory device 342 storing instructions defining an application 344. Execution of the instructions in the memory device 342 by the processor 340 cause the application 344 to perform the operations described herein. The processor 340 may include a microcontroller, a controller, an application specific integrated circuit ("ASIC"), a central processing unit included on one or more integrated circuits, etc. The memory device 342 may include any volatile or non-volatile data/instruction storage device. The memory device 342 may include, for example, flash memory, random-access memory ("RAM"), read-only memory ("ROM"), Electrically Erasable Programmable Read-Only Memory ("EEPROM"), etc.

The application 344 may comprise a stand-alone software application that uses native controls of the client device 204, known as an app. The application 344 may also include a software module. In some embodiments, the application 344 may include a web browser.

The application 344 is configured to provide medication dose preparation management in conjunction with the eyewear device 202. In the illustrated example, the application 344 is communicatively coupled to the pharmacy server 302 via a network 350 (e.g., a cellular and/or Internet network). The pharmacy server 302 is communicatively coupled to a first memory device 360 storing medication dose order files 362. Each dose order corresponds to a patient-specific prescription for a medication. Alternatively, a dose order may comprise a batch order or stock order for medication doses.

Figure 4:
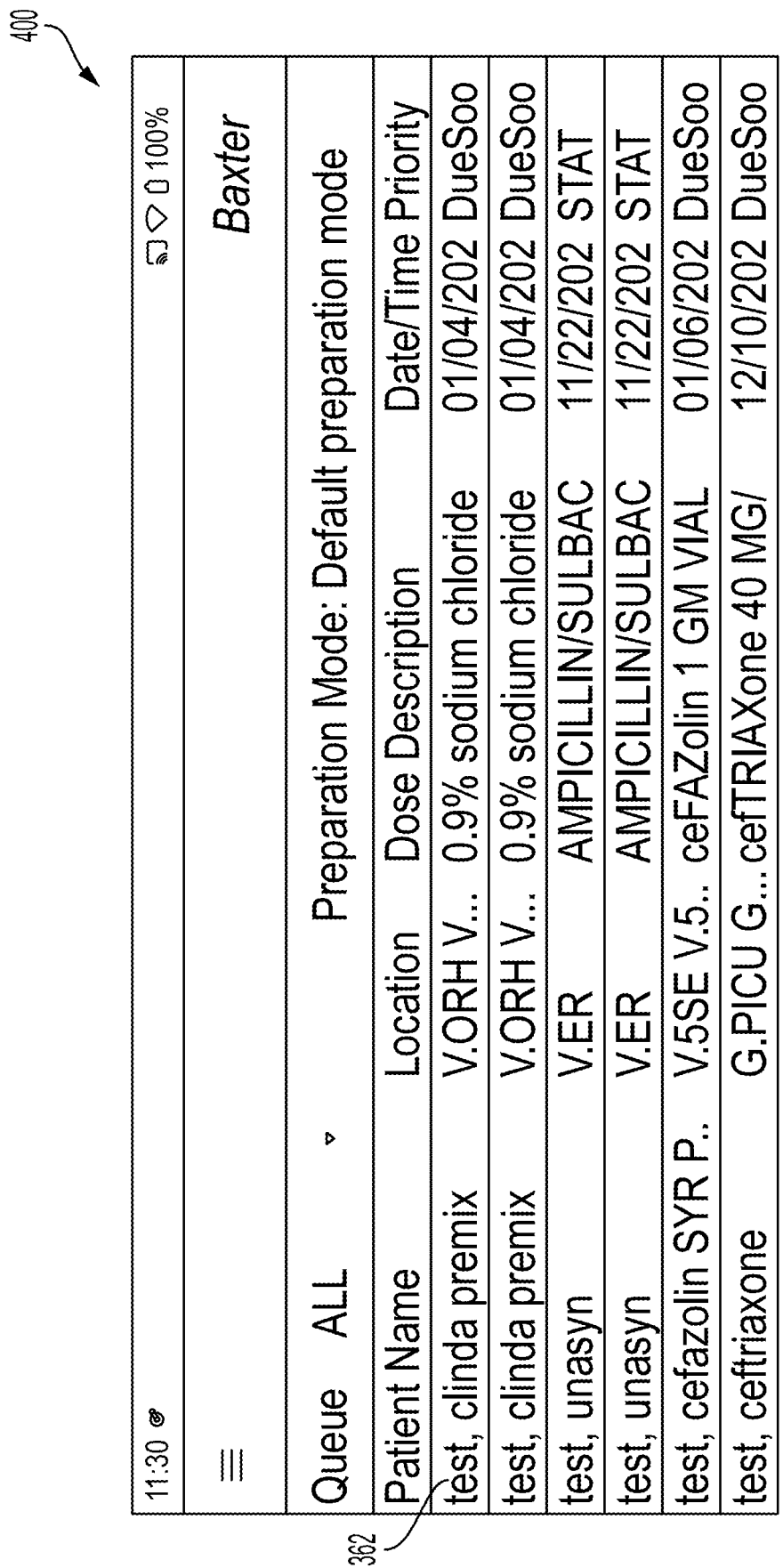
FIG. 4 is a diagram of a data structure or list that includes a plurality of dose orders, according to an example embodiment of the present disclosure.

FIG. 4 is a diagram of a data structure or list 400 that includes a plurality of dose orders 362, according to an example embodiment of the present disclosure. The dose order 362 includes a patient name or identifier, a hospital location (and/or room) of the patient, a dose description, a date/time of the order, and a priority. The dose description specifies a concentration or quantity of a specific formulation. The list 400 represents a queue of dose orders 362 managed by the pharmacy server 302. New dose orders 362 are added to the list 400 by the pharmacy server 302 as they are received from prescribing physicians. The pharmacy server 302 removes dose orders 362 from the list 400 after receiving an indication that a dose order is being prepared by a technician. In some embodiments, the pharmacy server 302 may move a dose order to an in-progress list, and then to a verification list after the medication dose has been prepared. Further, the pharmacy server 302 may move a dose order 362 from the verification list to a completed list after a pharmacist has verified the medication dose was prepared correctly.

Returning to FIG. 3, the application 344 is configured to access the list 400 from the pharmacy server 302 for display at the display screen 322 of the eyewear device 202. In some instances, the application 344 includes a user log-in and/or authentication feature. After a technician logs in to the application 344, the application 344 is configured to use the identity of the technical to request corresponding dose orders 362 among all dose orders received in the pharmacy server 302. For example, a technician may only be permitted to prepare certain medication doses or prepare medication doses for a certain location or floor in a hospital. The identifier of the technician is used to filter appropriate dose orders 362 for selection. The eyewear device 202 is configured to enable the technician to make a hands-free selection of a dose order 362 via a voice command, the touchpad, and/or a hand gesture recorded by the first camera module 316 or the second camera module 324. In addition to using the eyewear device 202, the application 344 is configured to accept inputs via the clinician device 204.

For voice commands, the application 344 is configured to convert audio received by the microphone into text using one or more speech-to-text algorithms. The application 344 then compares the text to a library of commands, such as "Select", "Open", "Next", "Confirm", "Cancel", "Record", "Scroll Down", "Enter", etc. Based on the matching command, the application 344 is configured to perform an operation with respect to a graphical user interface shown on the display screen 322, such as select a specified function or move a selection box/pointer. For voice entry of verification information, the application 344 first opens a text box then writes alphanumeric characters spoken by the technician to the text box.

For gestures, the first camera module 316 or the second camera module 324 record video or images of the technician's hand movements. Further, the sensor may record head movement. The video (or images) is analyzed by one or more algorithms of the application 344 to identify certain gestures. These identified gestures are compared to a library of gestures, which correspond to certain navigation commands and/or text entry commands. Similar comparisons are performed for angular acceleration data received from the sensor.

Figure 5:
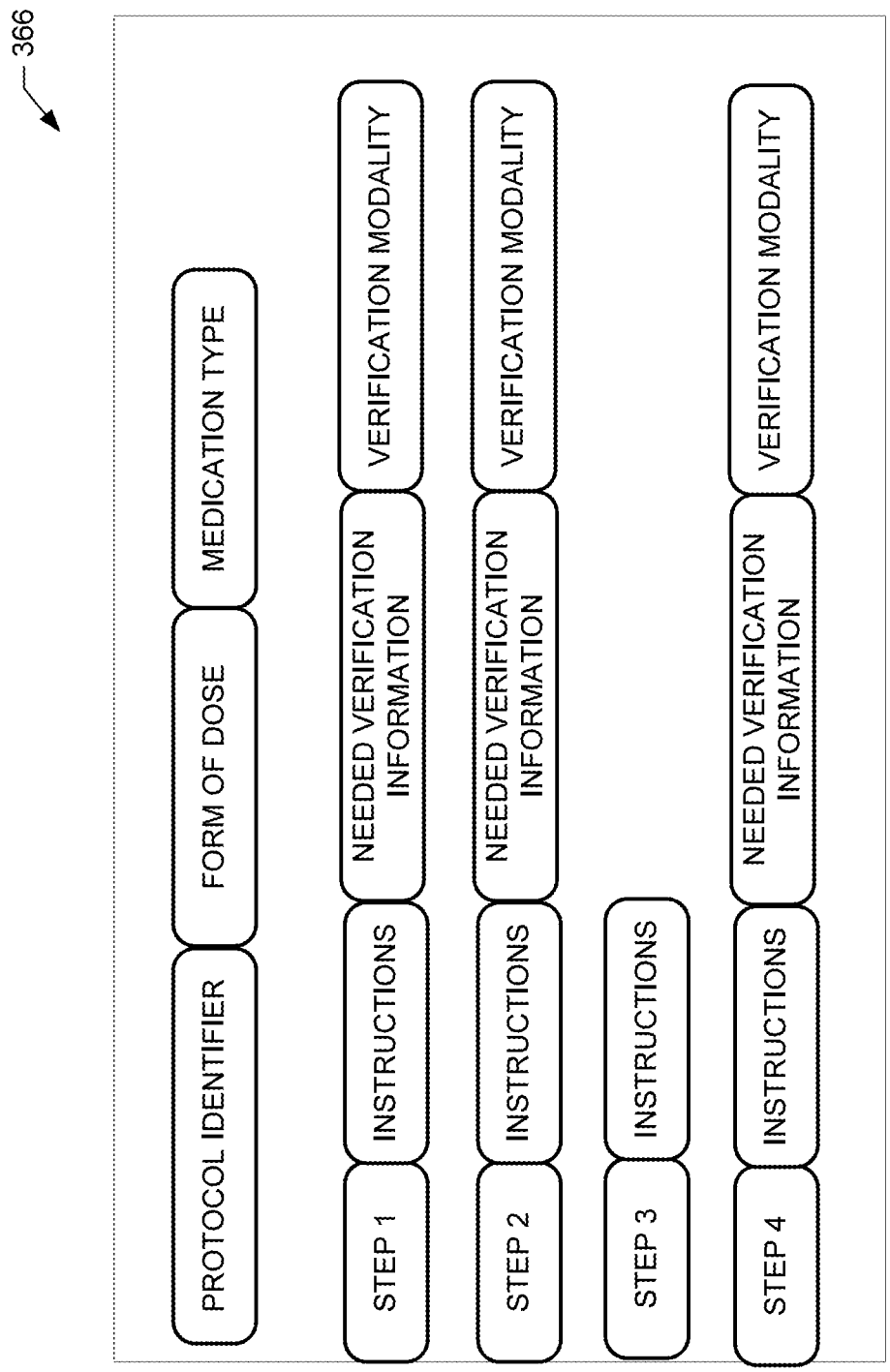
FIG. 5 is a diagram of an example preparation protocol for preparing a medication dose, according to an example embodiment of the present disclosure.

To prepare a medication dose to fulfill a dose order 362, the pharmacy server 302 provides access to preparation protocols 366, which are stored on a memory device 364. In some embodiments, the preparation protocols 366 are stored instead on the memory device 362. The preparation protocols 366 each defines a sequence of steps (e.g., graphical step instructions) for preparing a medication dose. FIG. 5 is a diagram of an example preparation protocol 366, according to an example embodiment of the present disclosure. The preparation protocol 366 may include a protocol identifier, a form of dose, and/or a medication type. The pharmacy server 302 may use the protocol identifier, the form of dose, and/or the medication type to determine which preparation protocol is needed for each dose order. For instance, after receiving a message from the application 344 on the client device 204 that is indicative of a selection of a dose order for ampicillin, the pharmacy server 302 searches the memory device 364 for the preparation protocol 366 that corresponds to ampicillin or a preparation protocol 366 that corresponds to a form of dosing for ampicillin (and similar medications). The pharmacy server 302 transmits the selected preparation protocol 366 to the application 344, which populates specific dose order information into the protocol, such as quantity or concentration. The application 344 then proceeds through the preparation protocol 366 in a step-wise manner until the end is reached.

In alternative embodiments, the pharmacy server 302 is configured to transmit all available preparation protocols 366 to the application 344, which may be stored in the memory device 342. In these alternative embodiments, the application 344 selects the appropriate preparation protocol 366. After selection, the application 344 populates the preparation protocol 366 with the dose order information.

As shown in FIG. 5, the preparation protocol 366 includes a sequential order of steps. Each step includes instructions or prompts that are displayed for a technician. In some embodiments, the instructions are formatted for display within the display screen 322 of the eyewear device 202. For example, the instructions are configured for a font size and spacing that enables viewing by a technician for the display screen 322, which is positioned relatively close to their eye. In some embodiments, the instructions may also include a second version that is configured for display on a screen of the client device 204. The second version of instructions may include more text, graphics, and/or other content that can be included in a relatively larger screen. The second content may also include links for tutorial videos or product monograph information, which may be too small for display on the display screen 322.

Figure 6:
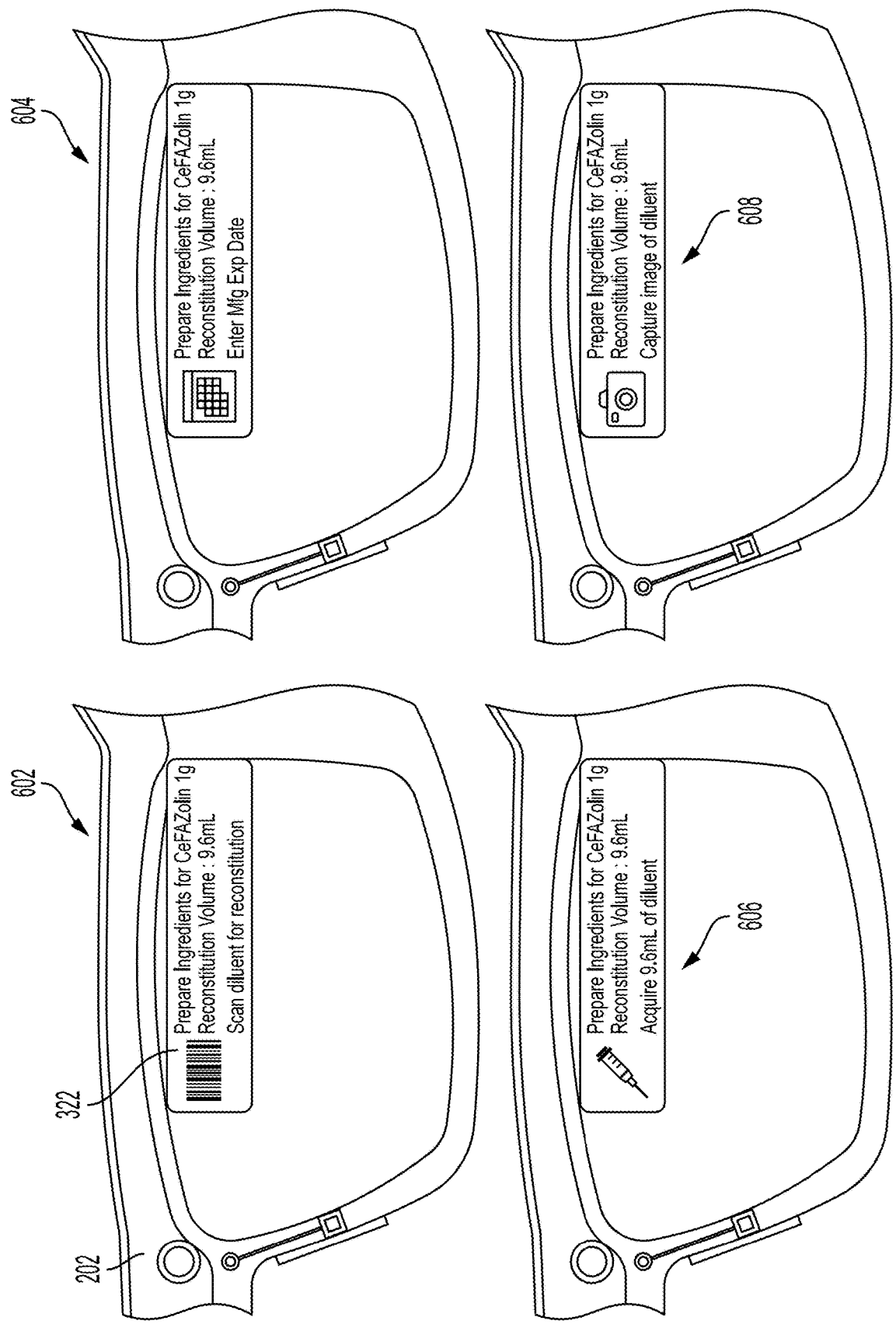
FIG. 6 is a diagram of example instructions displayed on a display screen of the eyewear device of FIGS. 2 and 3, according to example embodiments of the present disclosure.

FIG. 6 is a diagram of example instructions displayed on the display screen 322 of the eyewear device 202 of FIGS. 2 and 3, according to example embodiments of the present disclosure. In a first example 602, the instructions specify "Prepare ingredients for CeFAZolin 1 g Reconstitution Volume: 9.6 mL". The instructions also include an identification of needed verification information, which is prompted as "Scan diluent for reconstitution" and a picture of a barcode. The application 344 of the client device 204 creates a rendering of the instruction and prompts for the needed verification information from the corresponding step of the preparation protocol 366 shown in FIG. 5. The application 344 then transmits the rendering to the processor 326, which causes the image to be displayed on the display screen 322 of the eyewear device 202. In some instances, the text may be stored as an image, which is transmitted for display on the display screen 322.

A second example 604 includes the same instructions as the first example 602, but provides additional needed verification information for a manufacture expiration date. The second example 604 may correspond to a next step or a sub-step of the step shown in example 602. A third example 606 prompts a technician to acquire 9.6 mL of diluent and a fourth example 608 prompts the technician to capture an image of the diluent.

Returning to FIG. 5, in some embodiments each step may include a verification modality. For example, the modality may include a scan of a barcode, entry of information (such as a lot number or a value from the weight scale or balance 214), or a digital image. The presence of the verification modality provides a trigger, which when selected, causes the corresponding component of the eyewear device 202 to be activated.

FIG. 7 is a diagram of a user interface 700 that is displayed by the application 344 on the display screen 322 of the eyewear device 202, according to an example embodiment of the present disclosure. The user interface 700 includes a first section 702 that specifies the medication dose being prepared, which may be obtained from the dose order 326. Another section 704 of the user interface 700 specifies required ingredients needed for preparation, which is obtained from the corresponding preparation protocol 366. The user interface section 704 specifies the amount of ingredients needed and a total amount of each ingredient already obtained, as specified by verification information. The user interface 700 also includes a section 706 with the needed verification information and corresponding modalities.

Figure 8:
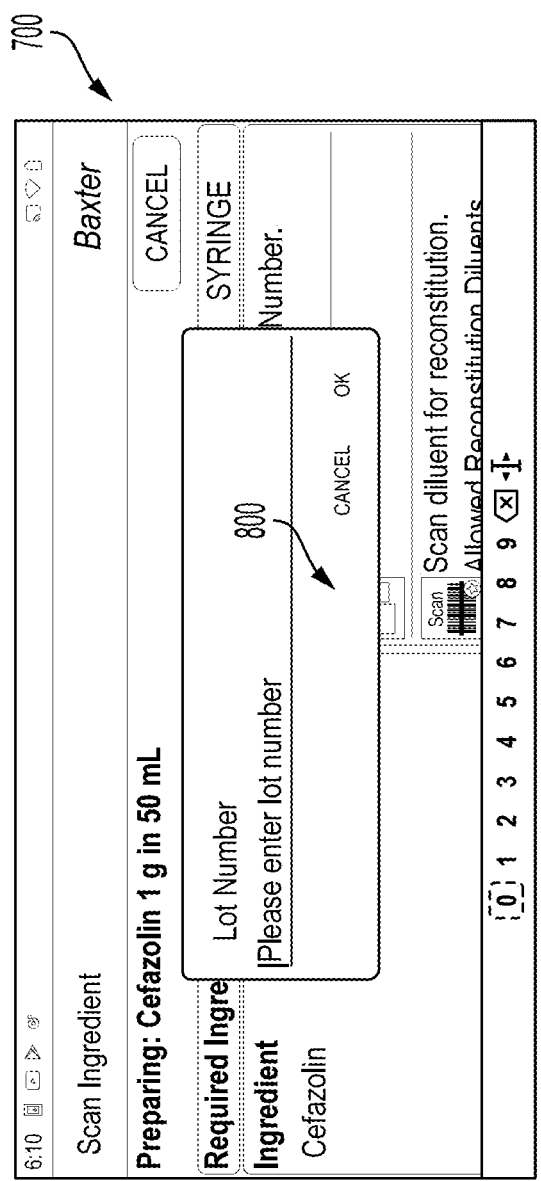
FIG. 8 is a diagram of a text box for verbally entering text to record verification information using the eyewear device of FIGS. 2 and 3, according to an example embodiment of the present disclosure.

The technician uses voice commands recorded by the microphone, hand gestures recorded by the cameras of the first or second camera modules 316 or 324, and/or uses a touchpad to select "Enter Product Lot Number". Selection of this verification option causes the application 344 to trigger the corresponding verification modality. As shown in FIG. 8, this includes the display of a text box 800. This also includes using microphone inputs to complete the text box. After the technician provides a verbal confirmation such as saying "ok", provides an approval gesture, uses the touchpad to move a pointer to "ok", or enters an input via the client device 204, the application 344 is configured to cause the user interface 700 to be displayed again with an indication that the lot number information (e.g., the verification information) has been recorded. Further, the entered verification information is stored to a verification file 346.

While not shown, prior to the operations described above, the technician may have previously performed a scan of a drug vial (ingredient barcode). This corresponds to the product lot number and expiration date shown in FIG. 7. In an alternative scenario, the technician may also be prompted to enter the lot and expiration date of a diluent that is being used to prepare a dose. The barcode scanner of the eyewear device 202 is automatically activated by the processor 326 and/or the application 344 to perform these scans.

Figure 9:
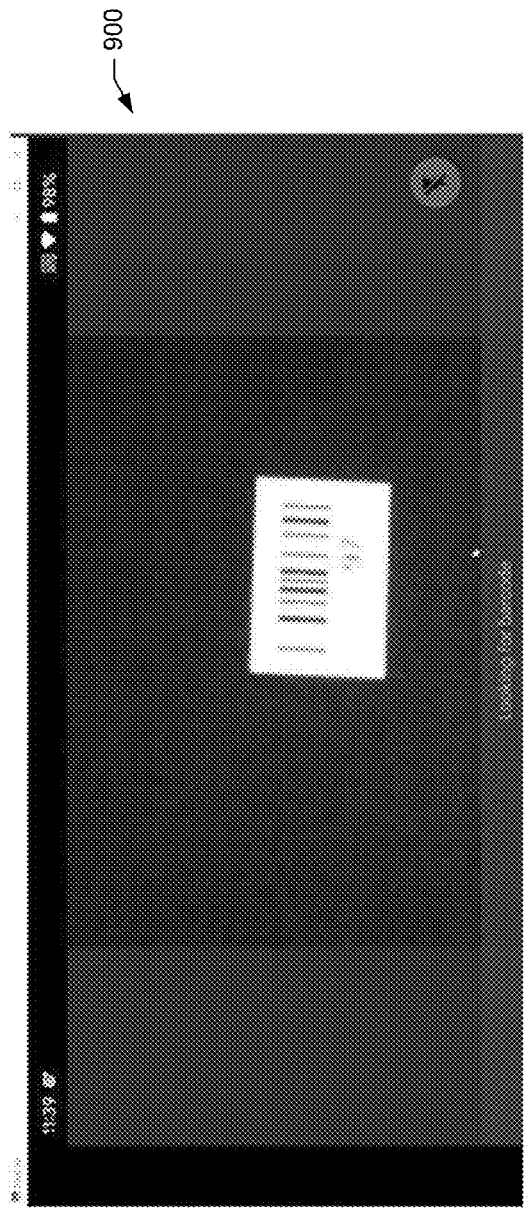
FIG. 9 is a diagram of a barcode, as recorded by a camera module of the eyewear device of FIGS. 2 and 3, according to an example embodiment of the present disclosure.

As shown in FIG. 7, the technician may select to scan a dose barcode. Selection of this verification modality causes the application 344 via the processor 326 to activate the barcode scanner of the eyewear device 202. FIG. 9 shows a view of a barcode, as recorded by the second camera module 324. In some embodiments, the laser may project a red light that shows a center of a field of view of the barcode scanner to help the technician align the second camera module 324 with the barcode. After scanning, the barcode data is transmitted to the application 344 for conversion into text. The application 344 marks the verification information as being obtained and stores the barcode data to the verification file 346 as verification information.

Figure 10:
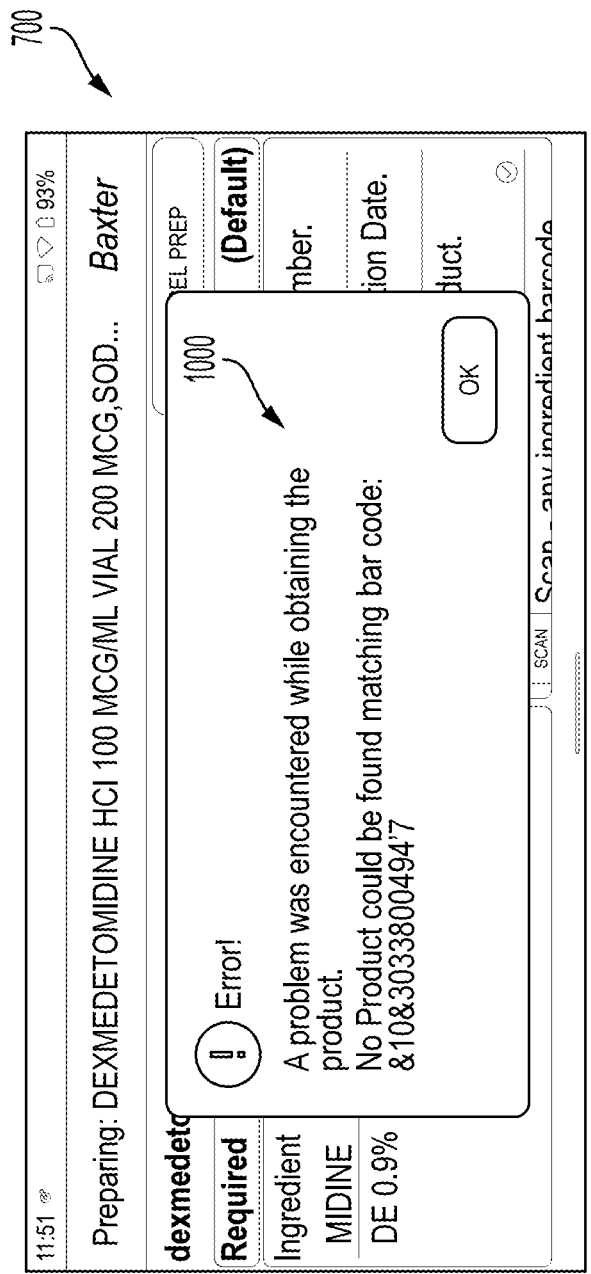
FIG. 10 is a diagram of an alert generated during preparation of a medication dose and displayed on a display screen of the eyewear device of FIGS. 2 and 3, according to an example embodiment of the present disclosure.

In some embodiments, the barcode identifies an ingredient name, a lot number, an expiration date, a concentration, and/or a quantity. The application 344 uses the needed verification information in the step of the preparation protocol to confirm the correct information was scanned. For example, the needed verification information may include ingredient names and approved name variations, an acceptable concentration range, and an acceptable quantity range. If data in the barcode does not match the needed verification information, the application 344 generates an alert 1000, as shown in FIG. 10. The application 344 may flag the step as being incomplete in the verification file 346 until the correct ingredient is scanned. Further, the application 344 may be configured to prevent the technician from progressing to a next step until the issue is resolved.

Returning to FIG. 3, as a technician progresses through the steps of the preparation protocol 366, verification information is stored to a verification file 346. The application 344 is configured to create and store the verification information to the verification file 346 during the preparation process. As discussed in more detail below, the verification file 346 is transmitted by the application 344 to the pharmacy server 302 after the preparation protocol 366 is completed or the technician ends the preparation prematurely. In some embodiments, the verification file 346 is discarded when a preparation is prematurely terminated. The pharmacy server 302 stores the verification file 346 to one of the memory devices 360 and 364 with other verification files for pharmacist review. The pharmacy server 302 may place the verification files in one or more queues for review, where the queue corresponds to completed/fulfilled dose orders for review.

For in-line verification, the verification file 346 is transmitted after certain designated steps (e.g., after completion of intermediary doses) during a preparation process to receive pharmacist review before a technician can continue. Upon approval, the dose will then appear back in a queue again for preparation. The technician selects a resume/complete option to finish preparing that dose. After the dose preparation is finished, the application 344 transmits the final pictures in the verification file 346 for the pharmacist review.

The pharmacy server 302 provides the verification file 346 to, for example, a pharmacist computer 370 to confirm or verify the medication dose was prepared properly and can be released to a patient. The pharmacist computer 370 may include an application or web browser that provides network access to the pharmacy server 302. The application or web browser may provide a dashboard for selecting a verification file 346 among the queue to review. The application or web browser also displays the verification information from the verification file 346 to enable a pharmacist to confirm a medication dose was prepared as required. In some embodiments, the pharmacist computer 370 is remote from a hospital pharmacy. Alternatively, the pharmacist computer 370 may be included within the hospital pharmacy. While the pharmacist computer 370 is shown as a laptop, in other examples the pharmacist computer 370 can include a smartphone, a tablet computer, a desktop computer, a workstation, etc.

Figure 11:
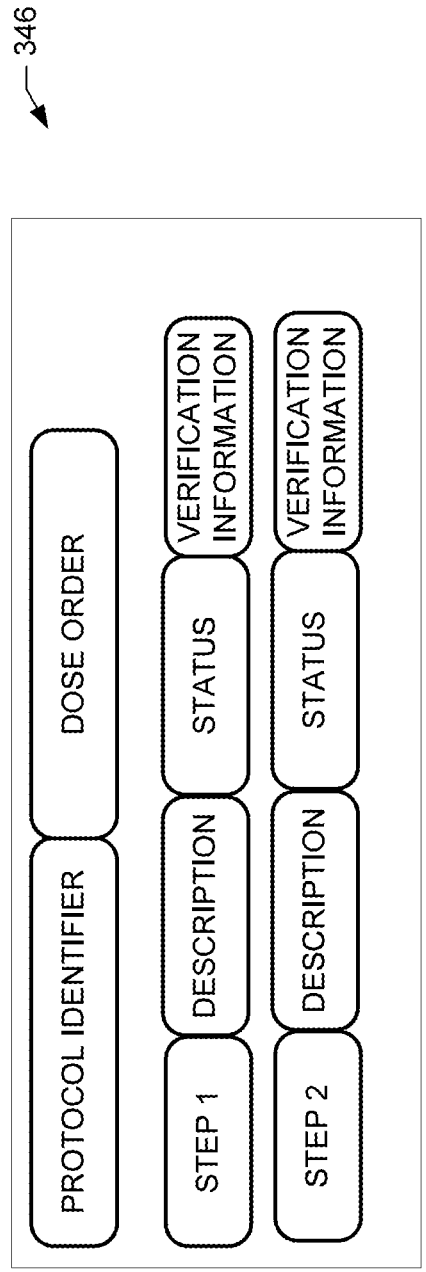
FIG. 11 is a diagram that is illustrative of contents of a verification file that may be created by an application and displayed on a pharmacist computer, according to an example embodiment of the present disclosure.
Figure 12:
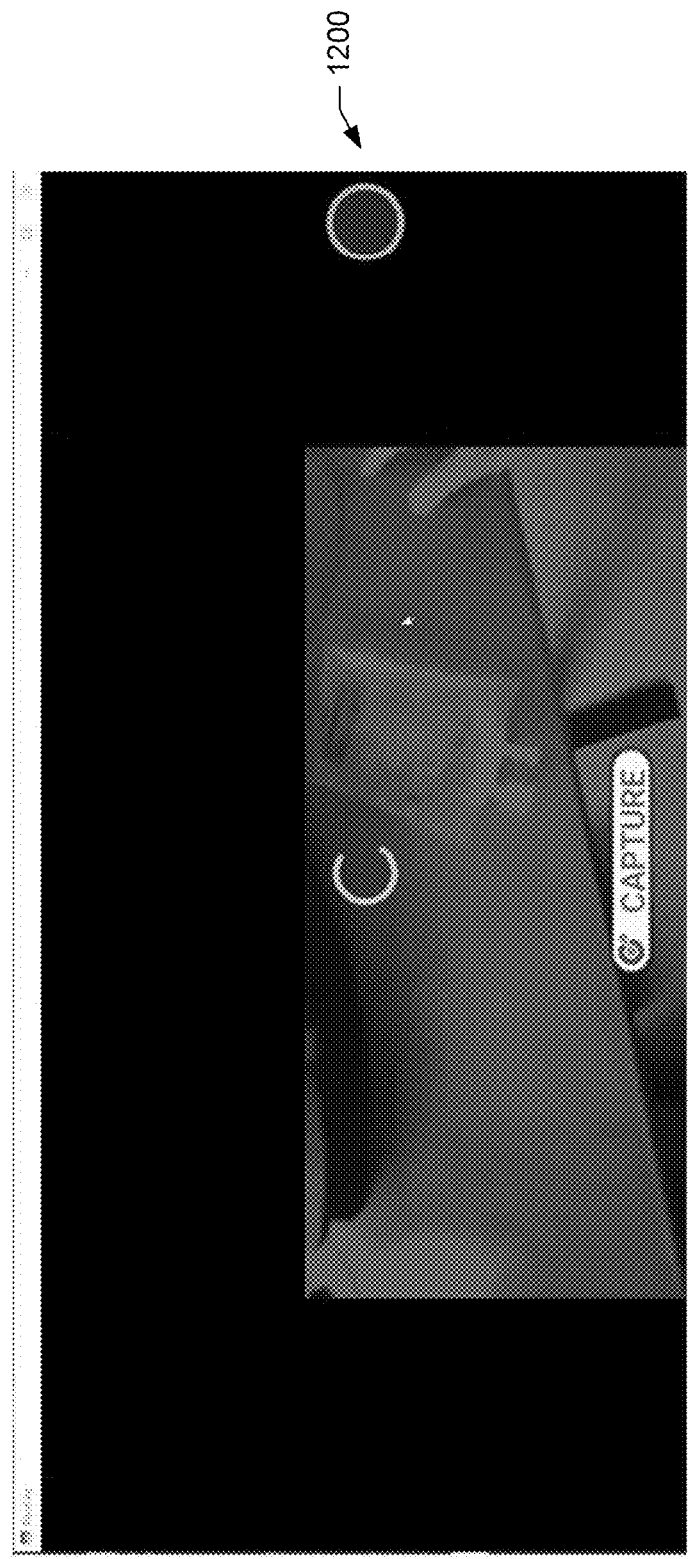
FIG. 12 is a diagram of a digital image recorded by a first camera module or a second camera module of the eyewear device, according to an example embodiment of the present disclosure.

FIG. 11 is a diagram that is illustrative of the verification information of the verification file 346 that may be created by the application 344 and displayed on the pharmacist computer 370, according to an example embodiment of the present disclosure. In the illustrated example, the verification file 346 identifies the preparation protocol 366 used for preparing the medication dose. The verification file 346 also includes or identifies the dose order. Further, the verification file 346 provides indications of at least some of the steps of the preparation protocol 366 that require verification. Each step may include a description of the requirement in addition to a flag indicative as to whether the step was completed by receiving verification information, which may include digital images, barcode data, confirmations entered by a technician, and text entered by a technician. FIG. 12 is a diagram of a digital image 1200 recorded by the first camera module 316 or the second camera module 324 of the eyewear device 202, according to an example embodiment of the present disclosure. The digital image 1200 shows an administration container comprising an IV bag with a medication formulation for administration to a patient. A pharmacist reviews the digital image 1200 to verify whether the administration container appears to be prepared correctly.

When a step has not been completed as required, a pharmacist uses the pharmacist computer 370 to flag the step in the verification file 346, which is transmitted to the pharmacy server 302. The application 344 is configured to receive a notification from the pharmacy server 302 that the verification file 346 has been reviewed and at least one step needs more attention or re-work. In some embodiments, setting the flag may cause contact information of the pharmacist to be included in the verification file 346. This contact information may be displayed in the display screen 322 of the eyewear device 202 when the step is reviewed by the technician. The technician may use voice commands, gestures, or the touchpad to select the contact information, which causes the application 344 to open a call function, email function, text message function, video call function, etc. (based on the modality of the contact information selected) of the client device 204 to interact with the pharmacist. The contact with the pharmacist can be made and conducted without the technician having to step away from the sterile dose preparation area of the laminar hood or BSC 212. Further, the pharmacist may use the pharmacist computer 370 to view live video from the first camera module 316 or the second camera module 324 to view the preparation of the medication dose from the perspective of the technician. The eyewear device 202 accordingly enables a technician to quickly contact a reviewing pharmacist to address questions about a prepared medication dose.

When the pharmacist confirms the medication dose was prepared properly, the pharmacist uses the computer 370 to store a flag to the verification file 346 indicative that the medication dose is approved. The updated verification file 346 is transmitted to the pharmacy server 302 (or updated at the server 302), which enables the medication dose to be released to a patient. In some embodiments, approval causes the printer 216 to print an administration label that is attached to an administration container. Alternatively, the approval enables the medication dose in the administration container to be checked out from the pharmacy for administration to a patient.

Medication Dose Preparation Embodiment

Figure 13A:
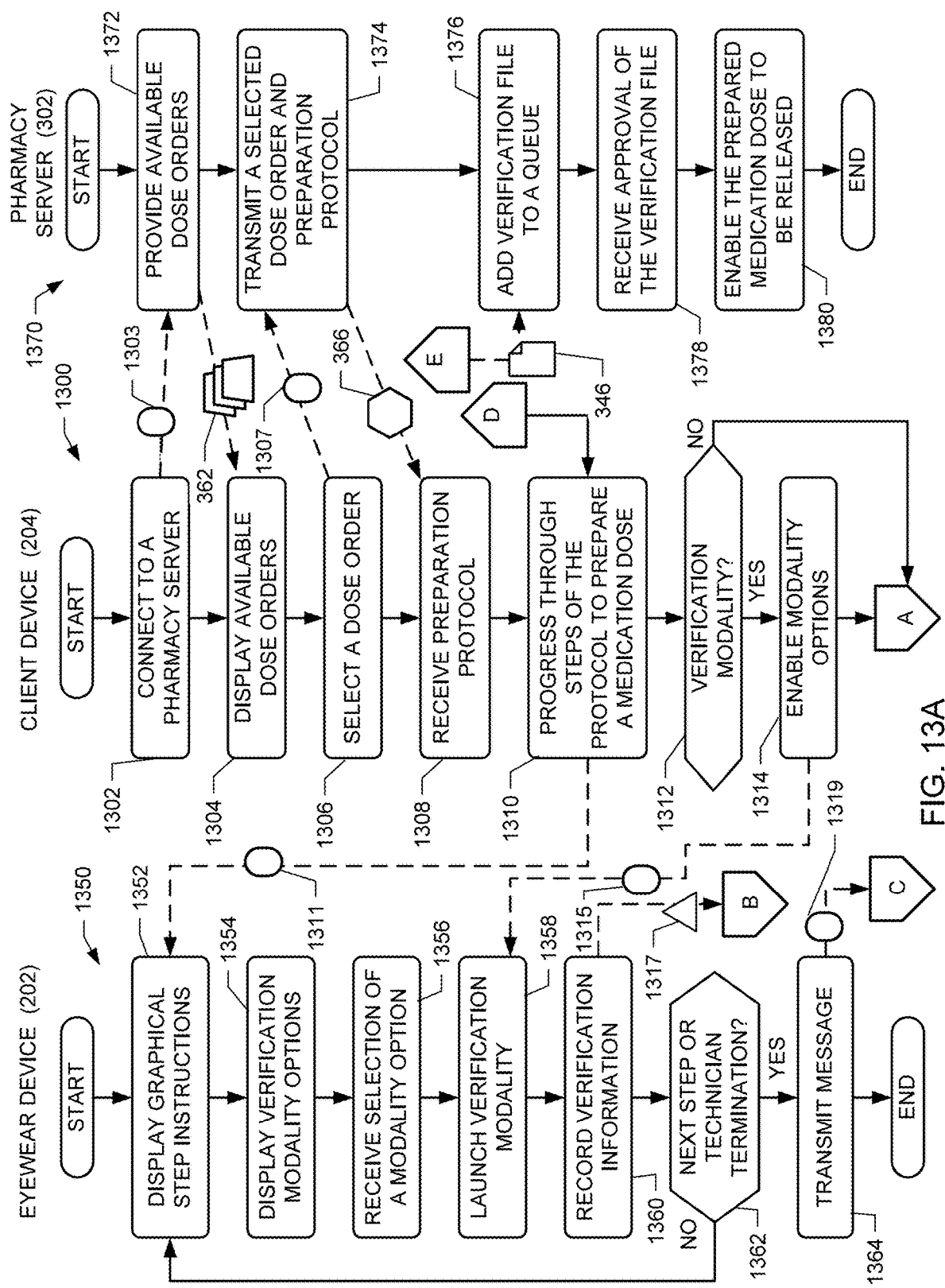
FIGS. 13A and 13B illustrate diagrams of example procedures for preparing a medication dose using the eyewear device and the client device of FIGS. 2 and 3, according to an example embodiment of the present disclosure.
Figure 13B:
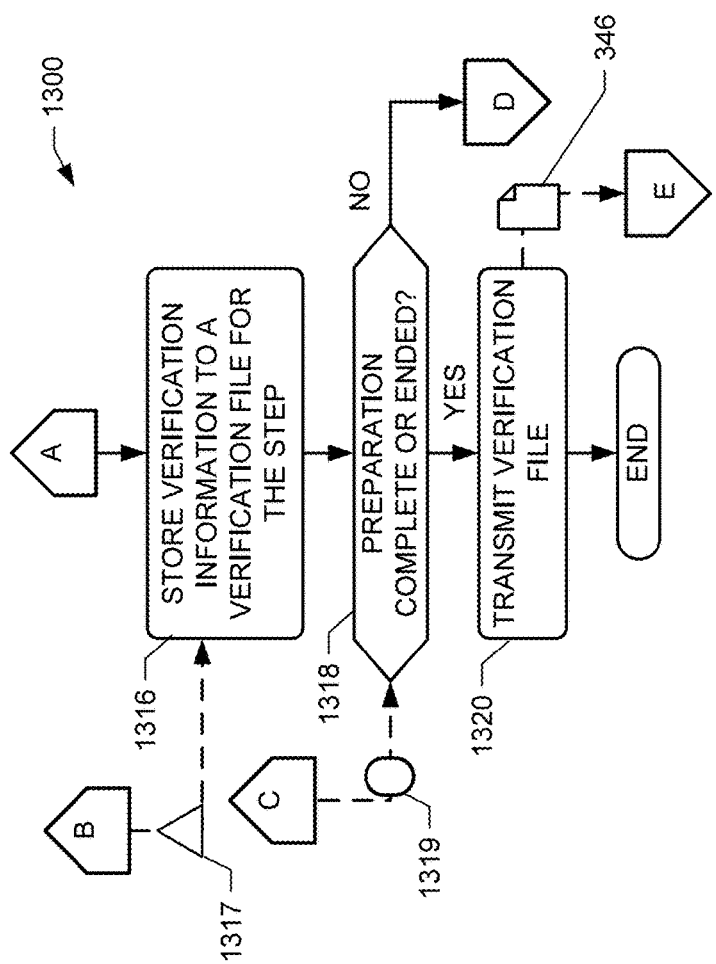

FIGS. 13A and 13B illustrate diagrams of example procedures 1300, 1350, and 1370 for preparing a medication dose using the eyewear device 202 and the client device 204 of FIGS. 2 and 3, according to an example embodiment of the present disclosure. Although the procedures 1300, 1350, and 1370 are described with reference to the flow diagrams illustrated in FIGS. 13A and 13B, it should be appreciated that many other methods of performing the acts associated with the procedures 1300, 1350, and 1370 may be used. For example, the order of many of the blocks may be changed, certain blocks may be combined with other blocks, and many of the blocks described are optional. For example, the procedure 1300 may include pre-use diagnostic check, such as ensuring the first camera module 316, the second camera module 324, and/or the microphone and speaker module 318 are operational and the eyewear device 202 is communicatively coupled to the client device 204. Further, a technician may be prompted to confirm there is sufficient battery life in the eyewear device 202 and/or the client device 204 for a preparation of a medication dose.

Figure 14:
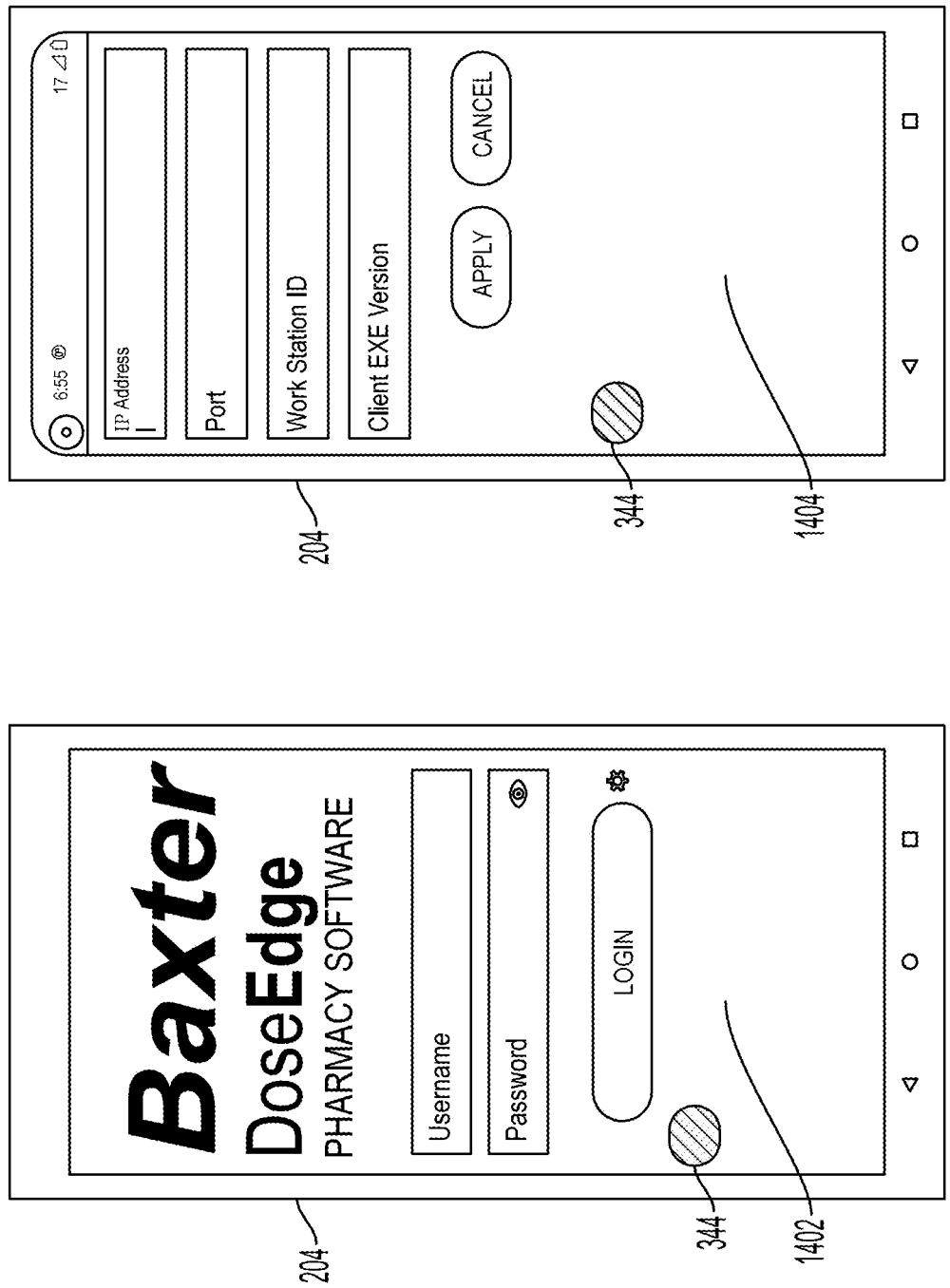
FIG. 14 is a diagram of example user interfaces that may be displayed by an application of the client device for connecting to the pharmacy server, according to an example embodiment of the present disclosure.

The example procedure 1300 begins when the application 344 on the client device 204 connects to the pharmacy server 302 (block 1302). Connecting to the pharmacy server 302 may include transmitting a message 1303 including a username and an identifier of a technician. FIG. 14 is a diagram of example user interfaces 1402 and 1404 that may be displayed by the application 344 of the client device 204 for connecting to the pharmacy server 302, according to an example embodiment of the present disclosure. The user interface 1402 prompts a technician for a username and password. The user interface 1404 prompts the technician for an IP address, port, workstation identifier, and a client executable version. The user interface 1404 may be displayed only for initial configuration and/or when the client device 204 connects via a different Wi-Fi network. The information entered by the technician into the user interfaces 1402 and 1404 may be included within the message 1303 transmitted to the pharmacy server 302 to establish a communication connection. In some embodiments, the user interfaces 1402 and 1404 may be displayed on the display screen 322 of the eyewear device 202, where voice commands may be used to enter the authentication/connectivity information.

Returning to FIG. 13A, the application 344 on the client device 204 next accesses the pharmacy server 302 to display a list or other data structure of dose orders 362, similar to the list 400 shown in FIG. 4 (block 1304). In some embodiments, text within the dose description field may automatically scroll to enable viewing of all the text in the field without having to open the field. In some instances, the list 400 may include a row number to enable easier voice selection. The application 344 on the client device 204 then receives a selection of a dose order 362 (block 1306). Selection may be made by sending a message 1307 to the pharmacy server 302 identifying the dose order or a row number. In response, the pharmacy server 302 determines a corresponding preparation protocol 366, which is transmitted to the application 344 (block 1308). The preparation protocol 366 is similar to the preparation protocol 366 described in conjunction with FIG. 5, for example.

Figure 15:
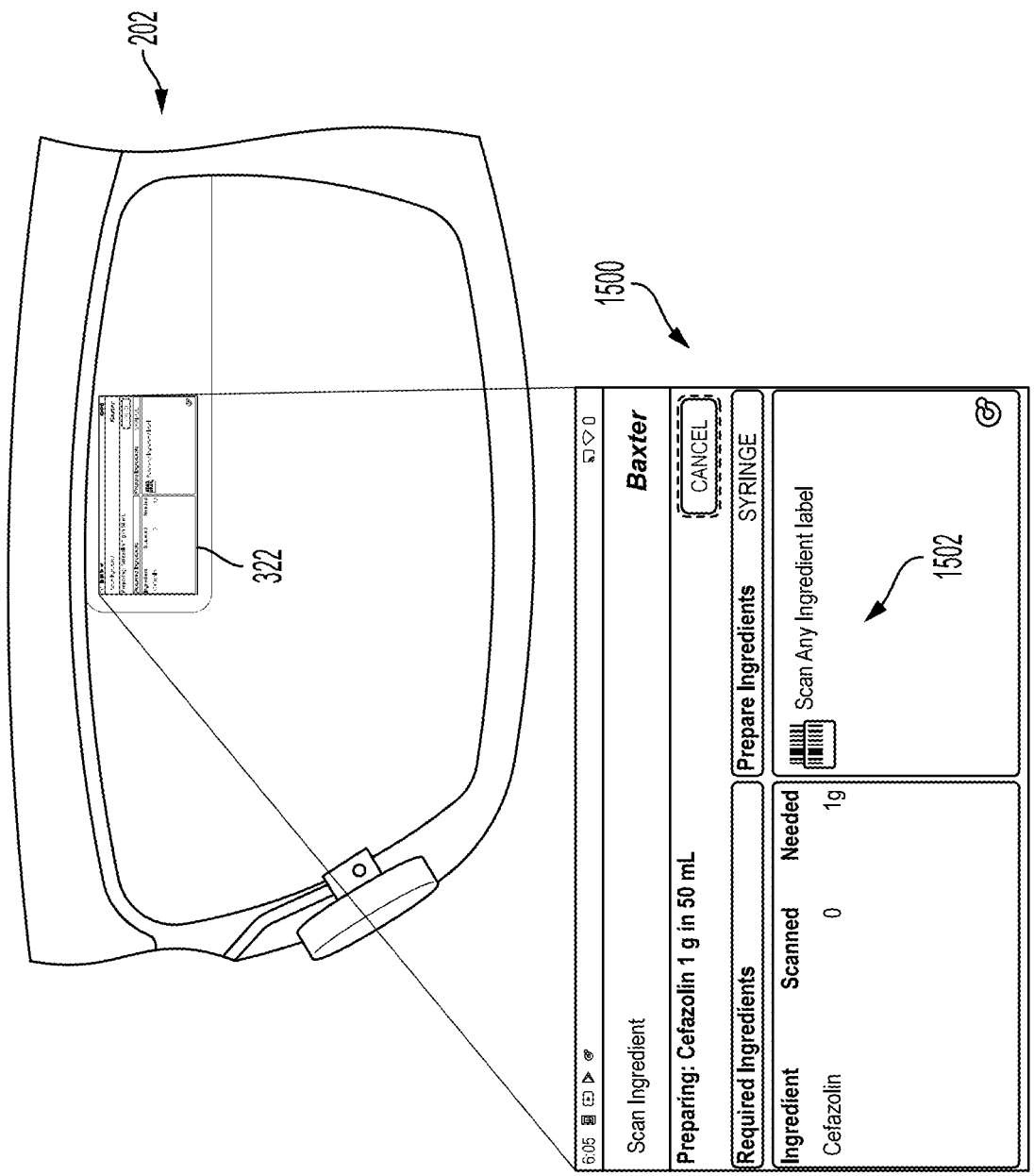
FIG. 15 shows a diagram of an example graphical user interface that is displayed on a display screen of the eyewear device, according to an example embodiment of the present disclosure.

The application 344 of the client device 204 next applies parameters from the selected dose order 362 to the preparation protocol 366 and sequentially progresses through the steps (block 1310). For each step, the application 344 identifies information needed for verification, and transmits one or more messages 1311 to the eyewear device 202 with graphical user interfaces for display on the display screen 322. FIG. 15 shows a diagram of an example graphical user interface 1500 that is displayed on the display screen 322 of the eyewear device 202, according to an example embodiment of the present disclosure. As shown, the user interface 1500 identifies the medication dose being prepared ("Cefazolin 1 g in 50 mL") in addition to a list of required ingredients. Section 1502 shows a prompt of the preparation protocol 1502 identifying needed verification information ("Scan Any Ingredient label").

Returning to FIG. 13A, the application 344 on the client device 204 determines if a verification modality is associated with the step of the preparation protocol 366 (block 1312). The verification modality may include text entry, confirmation from a technician, a barcode scan, a digital image, or video. If there is a modality associated with the step, the application 344 enables modality options for selection in the user interface 1500, for example (block 1314). This may include associating certain selections of verification options with a verification modality of the eyewear device 202. This may also include transmitting a message or signal 1315 from the application 344 to the eyewear device 202 to activate the modality (e.g., turn on the camera or barcode scanner). For text entry, the application 344 may cause a text box to be displayed on the display screen 322 and write characters as they are spoken until a verbal command word is received, such as "confirm" or "ok". In some embodiments, the verification modality is specified by the verification modality of the related step of the preparation protocol 366, as shown in FIG. 5

In an example, the user interface 1500 of FIG. 15 shows a single option for a barcode scan. The technician may provide a voice command via the eyewear device 202 to select the modality. The application 344 is configured to interpret the command and determine the command corresponds to selection of the verification modality in the section 1502 of the user interface 1500. The voice command may include the words "Scan" or "Scan Barcode". Based on the correspondence specified between the command terms and an operation to active the barcode scanner, the application 344 is configured to activate the barcode scanner and laser to enable the technician to perform a barcode scan.

In the example shown in FIG. 15, after a barcode label on an ingredient container is scanned, the application 344 receives data 1317 from the barcode scanner of the eyewear device 202. The application 344 converts the data into text, which corresponds to verification information. The application 344 may compare the verification information to specified (needed) verification information in the protocol 366 to confirm the verification information is correct (e.g., did the technician scan the right ingredient). If so, as shown in FIG. 13B, the application 344 sets a flag to indicate the step has been successfully completed and stores the verification information to a verification file 346 (block 1316). In some instances, the application 344 automatically advances to a next step in the preparation protocol sequence (without needing input from the technician) after confirming the verification information is within an acceptable range or otherwise matches the needed verification information that is specified in the preparation protocol 366.

When there is an error in the match, the application 344 prompts the technician to correct the error via one or more messages displayed on the display screen 322 of the eyewear device 202. The application 344 may prevent the technician from progressing to other steps until the current step is successfully completed. In some instances, after an error is issued, the application 344 may provide an option to contact a pharmacist for assistance, selection of which causes the client device 204 to establish the connection, all while the technician stays in the sterile dose preparation environment without having to physically contact the client device 204.

The application 344 of the client device 204 next determines if all of the steps of the protocol 366 have been completed and/or if a message 1319 has been received from the eyewear device 202 indicative that the technician is ending the preparation of the medication dose (block 1318). If the message 1319 was received or the steps have been completed, the application 344 transmits the verification file 346 to the pharmacy server 302 for pharmacist verification. The example procedure 1300 may then end. The procedure 1300 may restart at block 1310 when the pharmacist specifies one or more steps need re-work or rejects the preparation such that the medication dose needs to be prepared again. However, if the message 317 was not received or there are additional steps of the protocol 366, the procedure 1300 returns to block 1310 of FIG. 13A and performs the next step.

The example procedure 1350 begins when the eyewear device 202 receives the message 1311 from the application 344 on the client device 204 and displays one or more user interfaces with graphical step instructions and verification modality options (blocks 1352 and 1354). The eyewear device 202 next receives a selection of a modality option to provide verification information (block 1356). As discussed above, this can include a selection to perform a barcode scan, entry of text, a confirmation, a digital image, or a video. For a step where a container or ingredient needs to be weighed by the scale or balance 214, the verification option may include recording a picture of a display screen of the scale or balance 214 or verbally saying the weight.

Figure 16:
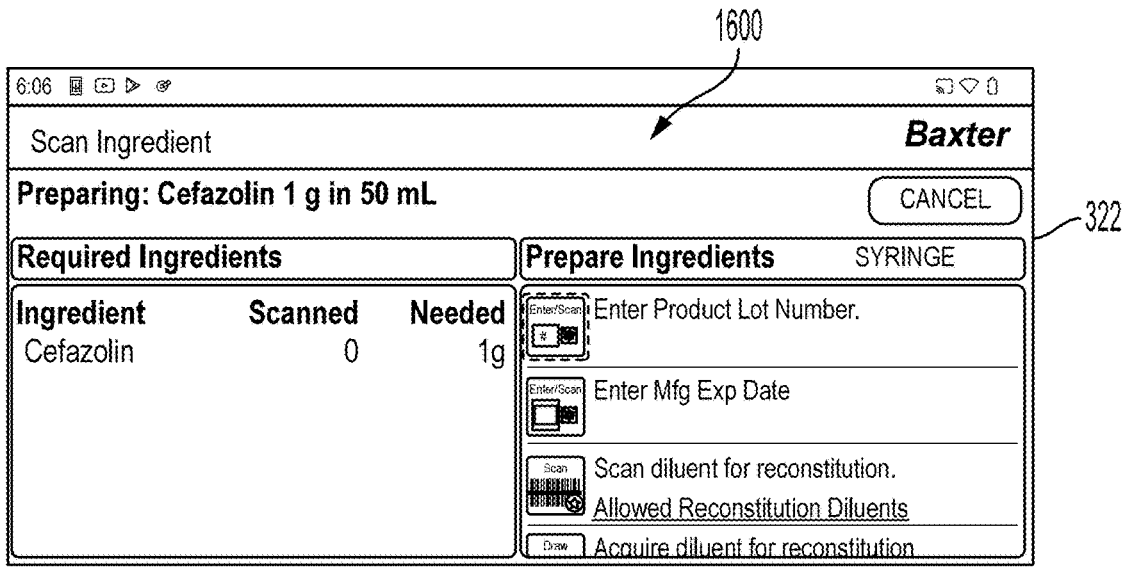
Figure 17:
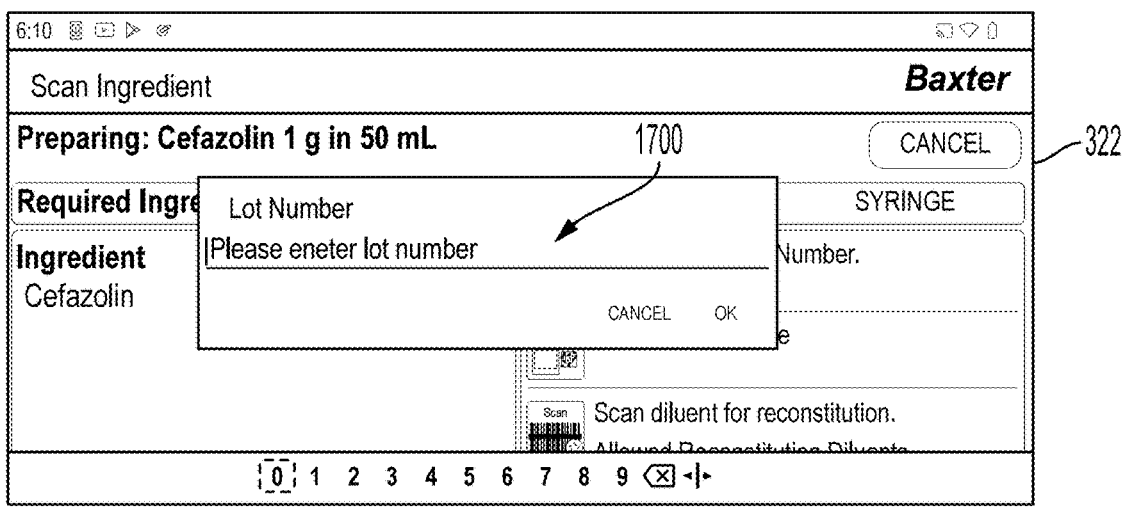
Figure 18:
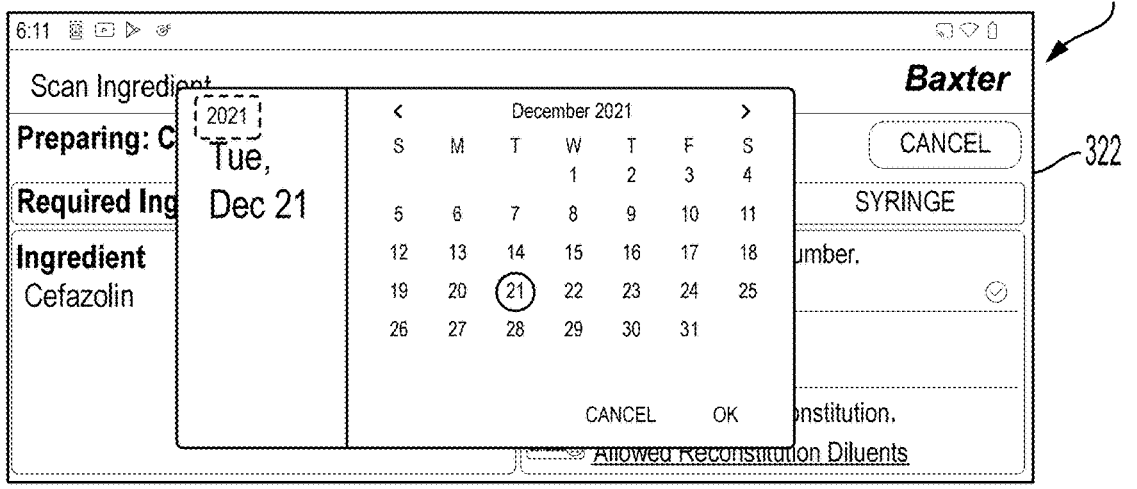

The eyewear device 202 next receives an instruction or message from the client device 204 to activate the modality (block 1358). The eyewear device 202 activates the modality and records data 1317, such as a barcode scan, a digital image, or video (block 1360). FIGS. 16 to 22 are diagrams of example graphical user interfaces corresponding to activated modalities of the eyewear device 202, according to example embodiments of the present disclosure. FIG. 16 shows that once a drug vial has been scanned, the application 344 prompts the technician to enter a product lot number, expiration date, and diluent. Selection of the lot number causes the application 344 to enter a text entry modality, such as text box 1700 in FIG. 17. The text box 1700 is displayed on the display screen of the eyewear device 202. Alphanumeric characters spoken by the technician are deciphered and written to the text box 1700 by the application 1700. This modality ends when the application 344 identifies a voice command such as "ok" or "complete". FIG. 18 is a user interface 1800 for entering an expiration date shown on an ingredient container. In this instance, the user interface 1800 is another text entry box shown as a calendar that is displayed by the application 344 after the user selects the expiration option. The application 344 processes voice entries received during this time as calendar inputs and accordingly shows the spoken expiration date on the user interface 1800. This modality ends when the application 344 identifies a voice command such as "ok" or "complete".

FIG. 19 shows the user interface 1600 after the product lot and expiration dates have been entered. The application 344 confirmed the data entered is within acceptable values and provides a visual indication of a check mark that the step/sub-step has been completed. FIG. 20 shows a user interface 2000 displayed by the display screen 322 when the technician selects the diluent entry section of the user interface 1600. The user interface 2000 prompts the technician to scan a barcode of a sterile water container, enter a diluent lot number, and an expiration date. The application 344 causes the corresponding modalities to be activated on the eyewear device 202 for receiving data that is converted by the application 344 into the verification information. In this example, the application 344 determines a container storing 20 mL of sterile water has been scanned and also determines that another 76 mL is needed. The application 344 may be configured to prevent the technician from progressing to a next step until the required volume of diluent has been scanned.

Figure 21:
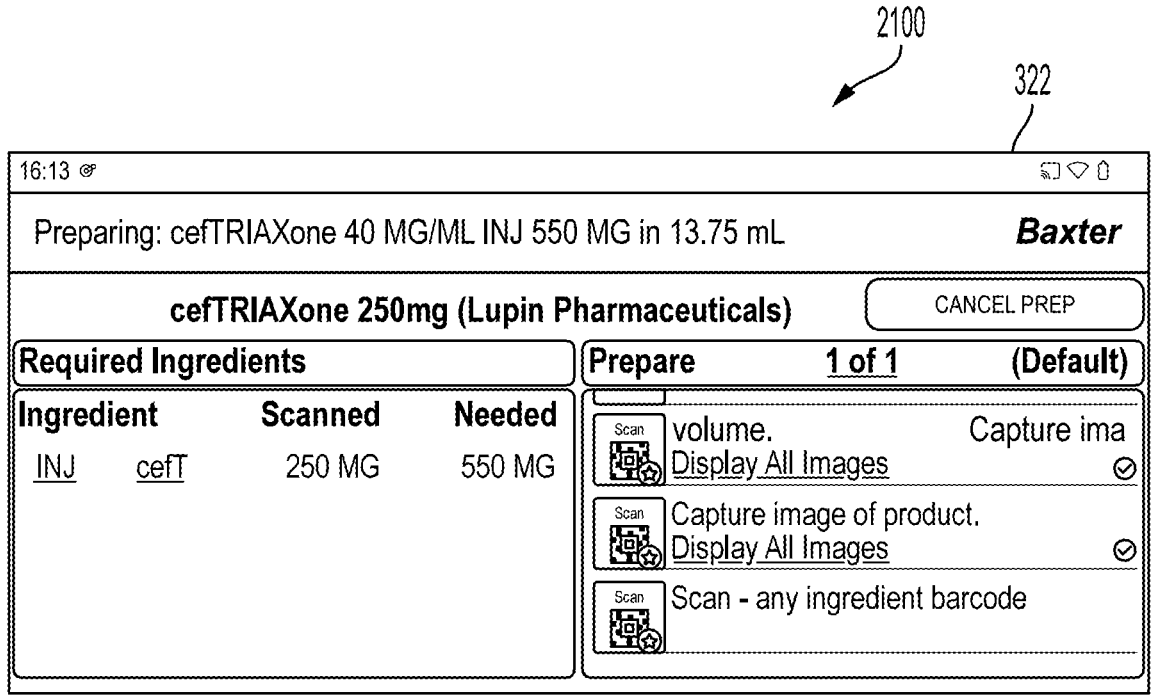
Figure 22:
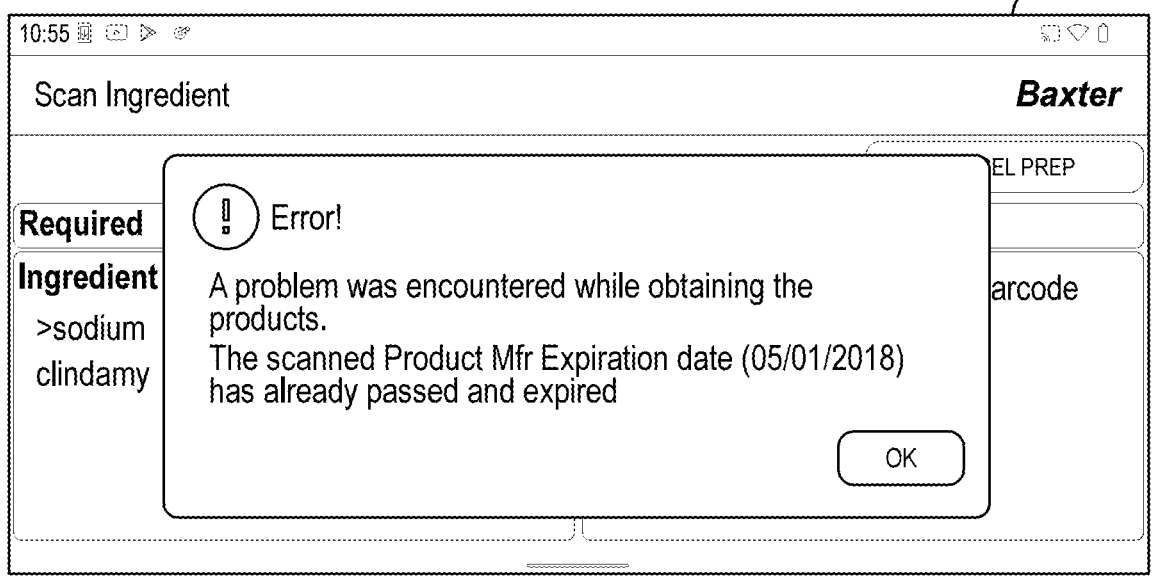

FIG. 21 shows a diagram of a user interface 2100 where only 250 mL of cefTRIAXone was scanned. The application 344 causes the "scan any barcode" prompt to be active in the user interface 2100 to indicate that additional quantities of cefTRIAXone are required to complete this step. The application 344 uses the needed verification information portion of the preparation protocol 366 (determined based on the dose order) to determine the amount needed for this step. FIG. 22 is a diagram of a user interface 2200 showing an error when the application 344 determines that verification information does not match the needed verification information of a protocol 366. In this example, the error displayed on the display screen 322 of the eyewear device 202 indicates that the technician scanned an ingredient container with an expired drug/diluent. The application 344 may prevent the technician from progressing to a next step until a drug/diluent is scanned with an acceptable expiration date.

Returning to FIGS. 13A and 13B, the data 1317 from the eyewear device 202 is transmitted to the application 344 for processing into verification information. The eyewear device 202 next determines if a next step is to be displayed on the display screen (block 1362). When a next step is to be displayed, the procedure 1350 returns to blocks 1352 and 1354 to display the corresponding graphical user interface. If instead a technician has entered an input to end the preparation session, the eyewear device 202 transmits a message 1319 with the input, which causes the application 344 to stop or pause preparation of the medication dose (block 1364). The example procedure 1350 then ends. The procedure 1350 may be restarted if the prepared dose is rejected or needs re-work after pharmacist verification.

The example procedure 1370 begins when the pharmacy server 302 receives a connection request message 1303 from the application 344 of the client device 204. After receiving the message 1303 with the authentication connection information, the pharmacy server 302 provides a list 400 of dose orders 362 that may be prepared by the technician (block 1372). The pharmacy server 302 may filter the dose orders based on a location and/or permission level of the technician. The pharmacy server 302 may provide the dose orders 362 for display on a dashboard in a list 400, as shown in FIG. 4.

After receiving a selection of a dose order from the application 344, the pharmacy server 302 determines a corresponding preparation protocol 366 (block 1374). The pharmacy server 302 may select the preparation protocol 366 based on a medication type or form of dose of the selected dose order 362. In some embodiments, the pharmacy server 302 applies parameters from the dose order 362, such as a concentration, a volume, or an amount, to the selected preparation protocol 366 to determine amounts of ingredients needed. Alternatively, the application 344 applies the dose order parameters to the protocol. The pharmacy server 302 transmits the preparation protocol 366 to the application on the client device 204.

After preparation of a medication dose corresponding to the selected dose order is complete, the pharmacy server 302 receives the verification file 346 from the application 344 (block 1376). The pharmacy server 302 adds the verification file 346 to a verification queue for pharmacists. After review, the pharmacy server 302 may receive an indication that the content of the verification file 346 has been approved (block 1378). The pharmacy server 302 accordingly enables the medication dose to be released to a patient and the procedure 1370 ends.

It should be appreciated that the procedures 1300, 1350, and 1370 may be configured to support in-line verification where certain steps of a preparation process are flagged as needing verification before a technician can move onto a next step. In these embodiments, the client device 204 is configured to transmit a verification file 346 to the pharmacy server 302 when verification information up to and including the designated step is received. When an approval message is received from the pharmacy server 302, the application 344 is configured to permit the technician to continue the preparation process, which may be paused until approval is received. In these instances, the application 344 moves the current preparation to a paused queue. Then, when a response from the pharmacy server 102 is received, the application 344 enables the preparation process to be selected to resume at a next step. The application 344 and/or the eyewear device 202 may display a notification when a message from the pharmacy server 102 is received.

In some embodiments, the pharmacy server 302 receives an indication that at least one step of the protocol provided in the verification file 346 needs re-work or that the preparation is rejected. In these instances, the pharmacy server 302 transmits the verification file 346, which may include comments and/or contact information of the reviewing pharmacist, to the client device 204. The technician receives a notification via the application 344 that the verification file 346 was returned. The technician may select the verification file 346 via the application 344 to view on the display screen 322 of the eyewear device 202 the one or more steps that need re-work. If the preparation is rejected, the application 344 causes the preparation protocol 366 to be restarted, with new verification information being stored by the application 344 on the original verification file 346 or a new verification file. The process continues until the mediation dose is prepared and verified by the pharmacist.

Remote Communication Embodiment

As discussed above, the eyewear device 202 enables a technician to contact a pharmacist or help center without having to leave the sterile dose preparation environment. If assistance is needed, the microphone of the eyewear device 202 records voice commands, which are deciphered and detected by the application 344. For example, the command "Call Pharmacist" is detected by the application 344 and causes the application 344 to place an audio or video call to the pharmacist. The technician may then communicate with the pharmacist hands-fee while continuing work in the sterile dose preparation environment and receiving assistance from the pharmacist. For video calls, video from the first camera module 316 or the second camera module 324 is transmitted by the application 344 to the pharmacist computer 370 to enable the pharmacist to view the same scene as viewed by the technician.

In addition to placing calls for assistance, the technician may use the eyewear device 202 to confirm ingredients in a medication closet or record pictures to demonstrate task compliance. Typically, a medication closet is in a non-sterile or semi-sterile environment. Instead of selecting ingredients and carrying the ingredients to the laminar hood or BSC 212 for scanning, the technician may scan labels on the ingredient containers at the supply area. Such a configuration provides instant feedback whether an ingredient is acceptable for use and saves the technician time from having to make multiple trips to the supply closet. In another example, a technician may use the eyewear device 202 to record the temperature and/or humidity of a cleanroom by capturing an image that will be date and time stamped when it is recorded and provided as part of the verification process.

HUD System Features

As discussed in detail above, the HUD system 200 is configured to perform the following operations:
Capture dose labels for IV solutions,
Recognize dose labels that cannot be prepared in the context of normal IV dose preparation (exceptional doses, e.g., TPN) and print out placeholder labels that are submitted for these doses,
Support dose preparation and labeling operations that do not require the use of a laminar air flow hood (such as assembly and/or activation of Mini-Bag Plus or ADD-Vantage bags),
Permit an authorized technician to schedule non-patient-specific dose preparation for production in a manual environment,
Permit an authorized technician to prepare products without associating the product with specific doses at the time of preparation,
Route each dose to be prepared to an appropriate workstation either as an automated workstation or a manual workstation,
Provide a summary display of pending work that allows a technician to determine the workload facing the IV room at any given time,
Workload may be directed to more than one workstation if it might be performed at any of several workstations. Performing of the work at one workstation shall remove the work from the queue of other workstations,
Workload may be reallocated by an authorized technician based on current or changing operating needs or available resources,
Presentation of work at an eyewear device accommodates the possibility that more than one technician is preparing doses at a workstation,
Alert the pharmacy technicians when a STAT or first dose order requires preparation and allow the automatic or manual escalation of priority for unprepared doses that will be needed soon,
Track and display the amount of time a pending STAT order has remained in the queue,
Maintain preparation instructions for each dose and display them to the pharmacy technician as need,
User interfaces should minimize the pharmacy technician interaction necessary to complete dose preparation,
Print labels for each dose manually prepared at a time near the completion of preparation when label application is appropriate,
Ensure that every dose is produced at a time that ensures the dose will still be potent at the time it is to be administered,
Use barcode technology to ensure that the ingredients in each dose are correct, diluted as needed with appropriate diluents, and are within their expiration dating,
Detect a difference between a vial that requires reconstitution before use and a vial that has already been reconstituted,
Maintain traceability to all commercial ingredients used to prepare a dose,
Generate a drug product and supplies requirements list for each workstation based on current workload,
Guide a technician through preparation of dilutions as needed to prepare pediatric doses,
Provide a mechanism to photograph intermediate containers in the preparation of a compounded sterile preparation for presentation to a verifying pharmacist,
Track user-specific, workstation-specific and area specific tasks, prompt for their completion, and record the results of their completion,
Display pending tasks with the time until they are due for completion,
Display of the eyewear device shall highlight any tasks that are due, or past-due for completion,
Track each dose individually from scheduling through delivery to the patient care area. Statuses shall include:
Pending
In-Process
Completed
Checked
Sorted Being delivered Delivered Discontinued Lost Damaged Permit an authorized technician to schedule preparation of a replacement dose when a dose is lost or damaged, Record and report the occurrence of lost/damaged doses, Provide a query tool that permits locating and determining the status of any arbitrary individual dose, Offer optional hardware modules for weighing final doses, reconstituting vials, and performing other tasks as may benefit from such automation, Configurable with email notifications that notify key individuals via email when the following occurs:
a. One or more stat orders has taken longer than a configured time limit to prepare,
b. The accumulated work for a given workstation has exceeded a limit set for that workstation,
c. A key task (such as cleaning the hood, replacing the pre-filter) has been allowed to lapse past its mandatory time,
d. A key maintenance item (such as hood certification) is due within a configured period of time,
e. The system has computed a daily production report for the previous day, or
f. Errors requiring attention occur in the interface software, Provide configurable reports that may be printed, displayed or exported to other document formats, Capture information necessary to permit a pharmacist at a remote location (a location other than the IV room) to check and verify a dose, Provide a portal through which a pharmacist at a remote location can check and verify a dose, Provide a mechanism by which labels can be printed for manual preparation if/when connectivity is lost for extended periods of time, Retain the original label feed for each dose and shall permit this feed to be used to produce dose labels, Support the representation of doses using the Institute for Safe Medication Practices ("ISMP") safety rules, Support the conversion of dose amounts between analogous units of measure to manage differences between ordered and provided dose units of measure, Permit communication with an authorized hospital information system, Accommodate the possibility that more than one pharmacist is checking and verifying doses at the same time, Be capable of receiving dose orders of various types from a Pharmacy Information System via an HL7 Interface or a Print Feed Interface, and transmitting dose information to outside systems via specified interfaces, and Be capable of receiving patient infusion status information from a medical gateway via standard interfaces, and allow the automatic or manual prioritization of the next queued dose of similar description for that patient.

Example Medication Dose Preparation Workflows

As discussed above, there are a plurality of preparation protocols 366 for preparing different types of medication doses. The following disclosure provides example steps for preparation protocols 366 that are executed on the application 344 of the client device 204 and the eyewear device 202.

Preparation of an Inhaler:
1. Pharmacy technician selects a dose in the queue from the eyewear device 202 using a voice or hand gesture command.
2. The application 344 prompts corresponding label to be printed for a final container application.
3. Pharmacy technician retrieves label.
4. Pharmacy technician retrieves product(s) required to complete drug preparation.
5. The application 344 displays information to pharmacy technician to prompt next action.
7. Pharmacy technician uses a voice command or hand gesture to trigger a scan of a source container for inhaler doses. Pharmacy technician scans the inhaler dose(s) to be prepared.
8. Sound alerts pharmacy technician that the scan was "captured" (not necessarily correctly).
8. The application 344 displays to the pharmacy technician if any barcode scans were incorrect.
9. Pharmacy technician prompts next step using a voice or hand gesture command.
10. The application 344 displays to the pharmacy technician to record a LOT and expiration date of the drug.
11. Pharmacy technician records the LOT and expiration date of the drug using a voice or hand gesture command.
12. Pharmacy technician prompts next step using a voice or hand gesture command.
13. The application 344 displays quantity of inhaler dose(s) to be prepared.
14. Pharmacy technician prompts next step using a voice or hand gesture command.
15. The application 344 prompts the pharmacy technician to take photo of the inhaler(s).
16. Pharmacy technician uses a voice command or hand gesture to capture an image.
17. The application 344 displays the image captured in the eyewear device 202.
18. Pharmacy technician reviews image.
19. Pharmacy technician prompts next step using a voice or hand gesture command.
20. The application 344 prompts the pharmacy technician to take a picture of a final container(s).
21. Pharmacy technician uses a voice command or hand gesture to capture an image.
22. Application 344 displays the image captured in the eyewear device 202.
23. Pharmacy technician reviews the image.
24. Pharmacy technician captures additional images (as needed) using the eyewear device 202.
25. Pharmacy technician prompts a next step using a voice or hand gesture command.
26. The application 344 prompts the pharmacy technician to scan a final container(s) preparation.
27. Pharmacy technician scans the final container(s) preparation.

Reconstitution and Admixing of Mitomycin:
1. Pharmacy technician selects a dose in a queue from the eyewear device 202 using a voice or hand gesture command.
2. The application 344 prompts the pharmacy technician to confirm a chilling block was stored upside down in a freezer overnight per recommended conditions, removed from freezer, and disinfected (action step).
3. Pharmacy technician accepts/confirms with a voice or hand gesture.

4. The application 344 prompts the pharmacy technician to confirm the chilling block is in the compounding area and they have completed the 20-minute wait time (action step).
5. Pharmacy technician accepts/confirms with voice or hand gesture.
6. The application 344 prompts corresponding label to be printed for a final container application.
7. Pharmacy technician retrieves the label.
8. The application 344 displays information to the pharmacy technician to remove drug vials from the chilling block
9. Pharmacy technician accepts/confirms with voice or hand gesture.
10. Pharmacy technician uses a voice command or hand gesture to trigger a scan of each vial(s) required for drug reconstitution.
11. Sound alerts the pharmacy technician that the scan was "captured" (not necessarily correctly).
12. The application 344 displays to the pharmacy technician if any barcode scans were incorrect.
13. Pharmacy technician requests next step using a voice or hand gesture command.
14. The application 344 prompts the pharmacy technician to record the LOT and expiration date of the drug.
15. Pharmacy technician records the LOT and expiration date of the drug using the voice or hand gesture command.
16. Pharmacy technician requests a next step using a voice or hand gesture command.
17. The application 344 prompts the pharmacy technician to attach a vial adaptor to 3 vials removed from chilling block (action step).
18. Pharmacy technician requests a next step using a voice or hand gesture command.
19. The application 344 prompts the pharmacy technician to connect syringe adaptor to one 10 mL syringe (action step).
20. Pharmacy technician requests a next step using a voice or hand gesture command.
21. The application 344 prompts the pharmacy technician to connect the syringe adaptor to a 20 mL syringe (action step).
22. Pharmacy technician requests a next step using a voice or hand gesture command.
23. The application 344 prompts the pharmacy technician to place 3 drug vials, a 10 mL, and a 20 mL syringe into chilling block for at least 10 minutes (action step).
24. Pharmacy technician requests a next step using a voice or hand gesture command.
25. The application 344 prompts the pharmacy technician to take a picture of components in the chilling block.
26. Pharmacy technician uses a voice command or hand gesture to capture an image.
27. The application 344 displays the image captured in the eyewear device 202.
28. Pharmacy technician reviews the image.
29. Pharmacy technician captures additional images (as needed) using the eyewear device 202.
30. Pharmacy technician requests a next step using a voice or hand gesture command.
31. The application 344 prompts the pharmacy technician to acquire a sterile water diluent (action step).
32. Pharmacy technician requests a next step using a voice or hand gesture command.
33. The application 344 prompts the pharmacy technician to take a picture of a diluent.
34. Pharmacy technician uses a voice command or hand gesture to capture an image.
35. The application 344 displays an image captured in the eyewear device 202.
36. Pharmacy technician reviews the image.
37. Pharmacy technician captures additional images (as needed).
38. Pharmacy technician requests a next step using a voice or hand gesture command.
39. The application 344 prompts the pharmacy technician to record the LOT and expiration date of the drug.
40. Pharmacy technician records the LOT and expiration date of the drug using a voice or hand gesture command.
41. Pharmacy technician requests a next step using a voice or hand gesture command.
42. The application 344 prompts the pharmacy technician to withdraw 2 mL of sterile water into a new 10 mL syringe.
43. Pharmacy technician requests a next step using a voice or hand gesture command.
44. The application 344 prompts the pharmacy technician to take a picture of sterile water.
45. Pharmacy technician uses a voice command or hand gesture to capture an image.
46. The application 344 displays the image captured by the eyewear device 202.
47. Pharmacy technician reviews the image.
48. Pharmacy technician captures additional images (as needed).
49. Pharmacy technician requests a next step using a voice or hand gesture command.
50. The application 344 prompts the pharmacy technician to withdraw 14 mL from a chilled hydrogel vial into a chilled 20 mL syringe and re-cap.
51. Pharmacy technician requests a next step using a voice or hand gesture command.
52. The application 344 prompts the pharmacy technician to take a picture of the syringe with hydrogel.
53. Pharmacy technician uses a voice command or hand gesture to capture an image.
54. The application 344 displays the image captured in the eyewear glasses 202.
55. Pharmacy technician reviews the image.
56. Pharmacy technician captures additional images (as needed).
57. Pharmacy technician requests a next step using a voice or hand gesture command.
58. The application 344 prompts the pharmacy technician to recap and place the 14 mL hydrogel syringe.
59. The application 344 prompts the pharmacy technician to take a picture of capped hydrogel syringe.
60. Pharmacy technician uses a voice command or hand gesture to capture an image.
61. The application 344 displays the image captured in the eyewear device 202.
62. Pharmacy technician reviews the image.
63. Pharmacy technician captures additional images (as needed).
64. Pharmacy technician requests a next step using a voice or hand gesture command.
65. The application 344 prompts the pharmacy technician to take a picture of the syringe in the chilling block.
66. Pharmacy technician uses a voice command or hand gesture to capture an image.
67. The application 344 displays the image captured in the eyewear device 202.

68. Pharmacy technician reviews the image.
69. Pharmacy technician captures additional images (as needed).
70. Pharmacy technician requests a next step using a voice or hand gesture command.
71. The application 344 prompts the pharmacy technician to withdraw 4 mL from the chilled hydrogel vial into the chilled 10 mL syringe.
72. Pharmacy technician requests a next step using a voice or hand gesture command.
73. The application 344 prompts the pharmacy technician to take a picture of the syringe with hydrogel.
74. Pharmacy technician uses a voice command or hand gesture to capture an image.
75. The application 344 displays the image captured by the eyewear device 202.
76. Pharmacy technician reviews the image.
77. Pharmacy technician captures additional images (as needed).
78. Pharmacy technician requests a next step using a voice or hand gesture command.
79. The application 344 prompts the pharmacy technician to discard the unused portion of hydrogel (action step).
80. Pharmacy technician requests a next step using a voice or hand gesture command.
81. The application 344 prompts the pharmacy technician to replace the needle on the sterile water syringe with a luer lock connector (action step).
82. Pharmacy technician requests a next step using a voice or hand gesture command.
83. The application 344 prompts the pharmacy technician to remove the syringe adaptor from the 4 mL hydrogel syringe (action step).
84. Pharmacy technician requests a next step using a voice or hand gesture command.
85. The application 344 prompts the pharmacy technician to connect the 4 mL hydrogel syringe to the other side of the luer lock connector on the sterile water syringe.
86. Pharmacy technician requests a next step using a voice or hand gesture command.
87. The application 344 prompts the pharmacy technician to take a picture of the connected syringes.
88. Pharmacy technician uses a voice command or hand gesture to capture an image.
89. The application 344 displays the image captured by the eyewear device 202
90. Pharmacy technician reviews the image.
91. Pharmacy technician captures additional images (as needed).
92. Pharmacy technician requests a next step using a voice or hand gesture command.
93. The application 344 prompts the pharmacy technician to gently mix the contents of both syringes by pushing the plungers of the syringes back and forth at least 25 times (action step).
94. Pharmacy technician requests a next step using a voice or hand gesture command.
95. The application 344 prompts the pharmacy technician to push entire contents of both syringes into a single syringe (action step).
96. Pharmacy technician requests a next step using a voice or hand gesture command.
97. The application 344 prompts the pharmacy technician to remove the luer lock connector and replace it on the full (6 mL) syringe with a new syringe adaptor.
98. Pharmacy technician requests a next step using a voice or hand gesture command.
99. The application 344 prompts the pharmacy technician to take a picture of the 6 mL syringe with the new syringe adaptor.
100. Pharmacy technician uses a voice command or hand gesture to capture an image.
101. The application 344 displays the image captured by the eyewear device 202.
102. Pharmacy technician reviews the image.
103. Pharmacy technician captures additional images (as needed).
104. Pharmacy technician requests a next step using a voice or hand gesture command.
105. The application 344 prompts the pharmacy technician to place the 6 mL syringe in the chilling block.
106. Pharmacy technician uses a voice command or hand gesture to capture an image.
107. The application 344 prompts the pharmacy technician to take a picture of the 6 mL syringe in the chilling block.
108. Pharmacy technician uses a voice command or hand gesture to capture an image.
109. The application 344 displays the image captured by the eyewear device.
110. Pharmacy technician reviews the image.
111. Pharmacy technician captures additional images (as needed).
112. Pharmacy technician requests a next step using a voice or hand gesture command.
113. The application 344 prompts the pharmacy technician to remove both drug vials from the chilling block (action step).
114. Pharmacy technician requests a next step using a voice or hand gesture command.
115. The application 344 prompts the pharmacy technician to gently tap the vials on the compounding surface to ensure contents are at the bottom (action step).
116. Pharmacy technician requests a next step using a voice or hand gesture command.
117. The application 344 prompts the pharmacy technician to remove the 6 mL syringe from the chilling block and inject 3 mL into the first drug vial.
118. Pharmacy technician requests a next step using a voice or hand gesture command.
119. The application 344 prompts the pharmacy technician to take a picture of drug vial.
120. Pharmacy technician uses a voice command or hand gesture to capture an image.
121. The application 344 displays the image captured by the eyewear device 202.
122. Pharmacy technician reviews the image.
123. Pharmacy technician captures additional images (as needed).
124. Pharmacy technician requests a next step using a voice or hand gesture command.
125. The application 344 prompts the pharmacy technician to inject remaining 3 mL of solution from syringe into the second drug vial.
126. Pharmacy technician requests a next step using a voice or hand gesture command.
127. The application 344 prompts the pharmacy technician to take a picture of drug vial.
128. Pharmacy technician uses a voice command or hand gesture to capture an image.
129. The application 344 displays the image captured by the eyewear device 202.
130. Pharmacy technician reviews the image.

131. Pharmacy technician captures additional images (as needed).
132. Pharmacy technician requests a next step using a voice or hand gesture command.
133. The application 344 prompts the pharmacy technician to gently swirl each upright vial at least 15 times WITHOUT inverting or shaking (action step).
134. Pharmacy technician requests a next step using a voice or hand gesture command.
135. The application 344 prompts the pharmacy technician to remove the syringe filled with 14 mL of liquid from the chilling block and inject 7 mL into the first drug vial.
136. Pharmacy technician requests a next step using a voice or hand gesture command.
137. The application 344 prompts the pharmacy technician to take a picture of drug vial.
138. Pharmacy technician uses a voice command or hand gesture to capture the image.
139. The application 344 displays the image captured by the eyewear device 202.
140. Pharmacy technician reviews the image.
141. Pharmacy technician captures additional images (as needed).
142. Pharmacy technician requests a next step using a voice or hand gesture command.
143. The application 344 prompts the pharmacy technician to inject the remaining 7 mL of solution from the syringe into the second drug vial.
144. Pharmacy technician requests a next step using a voice or hand gesture command.
145. The application 344 prompts the pharmacy technician to take a picture of the drug vial.
146. Pharmacy technician uses a voice command or hand gesture to capture the image.
147. The application 344 displays the image captured by the eyewear device 202.
148. Pharmacy technician reviews the image.
149. Pharmacy technician captures additional images (as needed).
150. Pharmacy technician requests a next step using a voice or hand gesture command.
151. The application 344 prompts the pharmacy technician to gently swirl each upright vial at least 15 times WITHOUT inverting or shaking (action step).
152. Pharmacy technician requests a next step using a voice or hand gesture command.
153. The application 344 prompts the pharmacy technician to recap and replace the 20 mL syringe in the chilling block.
154. The application 344 prompts the pharmacy technician to take a picture of capped 20 mL syringe.
155. Pharmacy technician uses a voice command or hand gesture to capture the image.
156. The application 344 displays the image captured by the eyewear device 202.
157. Pharmacy technician reviews the image.
158. Pharmacy technician captures additional images (as needed).
159. Pharmacy technician requests a next step using a voice or hand gesture command.
160. The application 344 prompts the pharmacy technician to take a picture of the 20 mL syringe in the chilling block.
161. Pharmacy technician uses a voice command or hand gesture to capture the image.
162. The application 344 displays the image captured by the eyewear device 202.
163. Pharmacy technician reviews the image.
164. Pharmacy technician captures additional images (as needed).
165. Pharmacy technician requests a next step using a voice or hand gesture command.
166. The application 344 prompts the pharmacy technician to recap and place both drug vials in the chilling block.
167. Pharmacy technician requests a next step using a voice or hand gesture command.
168. The application 344 prompts the pharmacy technician to take a picture of both vials in the chilling block.
169. Pharmacy technician uses a voice command or hand gesture to capture the image.
170. The application 344 displays the image captured by the eyewear device 202.
171. Pharmacy technician reviews the image.
172. Pharmacy technician captures additional images (as needed).
173. Pharmacy technician requests a next step using a voice or hand gesture command.
174. The application 344 prompts the pharmacy technician to wait 5 minutes (action step).
175. Pharmacy technician requests a next step using a voice or hand gesture command.
176. The application 344 prompts the pharmacy technician to remove both vials from the chilling block and vigorously swirl both vials upright at least 15 times (action step-1).
177. Pharmacy technician requests a next step using a voice or hand gesture command.
178. The application 344 prompts the pharmacy technician to place both drug vials back in the chilling block.
179. Pharmacy technician requests a next step using a voice or hand gesture command.
180. The application 344 prompts the pharmacy technician to take a picture of both vials in the chilling block.
181. Pharmacy technician uses a voice command or hand gesture to capture the image.
182. The application 344 displays the image captured by the eyewear device 202.
183. Pharmacy technician reviews the image.
184. Pharmacy technician captures additional images (as needed).
185. Pharmacy technician requests a next step using a voice or hand gesture command.
186. The application 344 prompts the pharmacy technician to wait 5 minutes (action step).
187. Pharmacy technician requests a next step using a voice or hand gesture command.
188. The application 344 prompts the pharmacy technician to remove both vials from the chilling block and vigorously swirl both vials upright at least 15 times (action step-2).
189. Pharmacy technician requests a next step using a voice or hand gesture command.
190. The application 344 prompts the pharmacy technician to place both drug vials back in the chilling block.
191. Pharmacy technician requests a next step using a voice or hand gesture command.
192. The application 344 prompts the pharmacy technician to take a picture of both vials in the chilling block.
193. Pharmacy technician uses a voice command or hand gesture to capture the image.

194. System displays the image captured by the eyewear device 202.
195. Pharmacy technician reviews the image.
196. Pharmacy technician captures additional images (as needed).
197. Pharmacy technician requests a next step using a voice or hand gesture command.
198. The application 344 prompts the pharmacy technician to wait 5 minutes (action step).
199. Pharmacy technician requests a next step using a voice or hand gesture command.
200. The application 344 prompts the pharmacy technician to remove both vials from the chilling block and vigorously swirl both vials upright at least 15 times (action step-3).
201. Pharmacy technician requests a next step using a voice or hand gesture command.
202. The application 344 prompts the pharmacy technician to place both drug vials back in the chilling block.
203. Pharmacy technician requests a next step using a voice or hand gesture command.
204. The application 344 prompts the pharmacy technician to take a picture of both vials in the chilling block.
205. Pharmacy technician uses a voice command or hand gesture to capture the image.
206. The application 344 displays the image captured by the eyewear device 202.
207. Pharmacy technician reviews the image.
208. Pharmacy technician captures additional images (as needed).
209. Pharmacy technician requests a next step using a voice or hand gesture command.
210. The application 344 prompts the pharmacy technician to wait 5 minutes (action step).
211. Pharmacy technician requests a next step using a voice or hand gesture command.
212. The application 344 prompts the pharmacy technician to remove both vials from the chilling block and vigorously swirl both vials upright at least 15 times (action step-4).
213. Pharmacy technician requests a next step using a voice or hand gesture command.
214. The application 344 prompts the pharmacy technician to place both drug vials back in the chilling block.
215. Pharmacy technician requests a next step using a voice or hand gesture command.
216. The application 344 prompts the pharmacy technician to take a picture of both vials in the chilling block.
217. Pharmacy technician uses a voice command or hand gesture to capture the image.
218. The application 344 displays the image captured by the eyewear device 202.
219. Pharmacy technician reviews the image.
220. Pharmacy technician captures additional images (as needed).
221. Pharmacy technician requests a next step using a voice or hand gesture command.
222. The application 344 prompts the pharmacy technician to wait 5 minutes (action step).
223. Pharmacy technician requests a next step using a voice or hand gesture command.
224. The application 344 prompts the pharmacy technician to remove both vials from the chilling block and vigorously swirl both vials upright at least 15 times (action step-5).
225. Pharmacy technician requests a next step using a voice or hand gesture command.
226. The application 344 prompts the pharmacy technician to place both drug vials back in the chilling block.
227. Pharmacy technician requests a next step using a voice or hand gesture command.
228. The application 344 prompts the pharmacy technician to take a picture of both vials in the chilling block.
229. Pharmacy technician uses a voice command or hand gesture to capture the image.
230. The application 344 displays the image captured by the eyewear device 202.
231. Pharmacy technician reviews the image.
232. Pharmacy technician captures additional images (as needed).
233. Pharmacy technician requests a next step using a voice or hand gesture command.
234. The application 344 prompts the pharmacy technician to wait 5 minutes (action step).
235. Pharmacy technician requests a next step using a voice or hand gesture command.
236. The application 344 prompts the pharmacy technician to remove both vials from the chilling block and vigorously swirl both vials upright at least 15 times (action step-6).
237. Pharmacy technician requests a next step using a voice or hand gesture command.
238. The application 344 prompts the pharmacy technician to place both drug vials back in the chilling block.
239. Pharmacy technician requests a next step using a voice or hand gesture command.
240. The application 344 prompts the pharmacy technician to take a picture of both vials in the chilling block.
241. Pharmacy technician uses a voice command or hand gesture to capture the image.
242. The application 344 displays the image captured by the eyewear device 202.
243. Pharmacy technician reviews the image.
244. Pharmacy technician captures additional images (as needed).
245. Pharmacy technician requests a next step using a voice or hand gesture command.
246. The application 344 prompts the pharmacy technician to wait 5 minutes (action step).
247. Pharmacy technician requests a next step using a voice or hand gesture command.
248. The application 344 prompts the pharmacy technician to remove one vial from the chilling block and vigorously swirl vial upright at least 15 times (action step).
249. Pharmacy technician requests a next step using a voice or hand gesture command.
250. The application 344 prompts the pharmacy technician to remove the 20 mL syringe from the chilling block (action step).
251. Pharmacy technician requests a next step using a voice or hand gesture command.
252. The application 344 prompts the pharmacy technician to withdraw 7 mL of solution from the drug vial using the chilled 20 mL syringe.
253. Pharmacy technician requests a next step using a voice or hand gesture command.
254. The application 344 prompts the pharmacy technician if unable to withdraw the full 7 mL amount to place back in chilling block and re-attempt (action step).
255. Pharmacy technician requests a next step using a voice or hand gesture command.

256. The application 344 prompts the pharmacy technician to take a picture of the drug vial.
257. Pharmacy technician uses a voice command or hand gesture to capture the image.
258. The application 344 displays the image captured by the eyewear device 202.
259. Pharmacy technician reviews the image.
260. Pharmacy technician captures additional images (as needed).
261. Pharmacy technician requests a next step using a voice or hand gesture command.
262. The application 344 prompts the pharmacy technician to remove the remaining vial from the chilling block (action step).
263. Pharmacy technician requests a next step using a voice or hand gesture command.
264. The application 344 prompts the pharmacy technician to inject 7 mL of solution from the 20 mL syringe into the $2^{nd}$ drug vial (action step).
265. Pharmacy technician requests a next step using a voice or hand gesture command.
266. The application 344 prompts the pharmacy technician to take a picture of the drug vial.
267. Pharmacy technician uses a voice command or hand gesture to capture the image.
268. The application 344 displays the image captured by the eyewear device 202.
269. Pharmacy technician reviews the image.
270. Pharmacy technician captures additional images (as needed).
271. Pharmacy technician requests a next step using a voice or hand gesture command.
272. The application 344 prompts the pharmacy technician to recap the $2^{nd}$ drug vial using the adaptor and vigorously swirl vial at least 15 times without inverting or shaking (action step).
273. Pharmacy technician requests a next step using a voice or hand gesture command.
274. The application 344 prompts the pharmacy technician to take a picture of the drug vial.
275. Pharmacy technician uses a voice command or hand gesture to capture the image.
276. The application 344 displays the image captured by the eyewear device 202
277. Pharmacy technician reviews the image.
278. Pharmacy technician captures additional images (as needed).
279. Pharmacy technician requests a next step using a voice or hand gesture command.
280. The application 344 prints a secondary preparation label with a printer based on when dose preparation was completed.
281. Pharmacy technician requests a next step using a voice or hand gesture command.
282. The application 344 prompts the pharmacy technician to apply the final container label to the drug vial and dispense in a light protective bag (action step).
283. The application 344 prompts the pharmacy technician to take a picture of the prepared drug in the light protective bag.
284. Pharmacy technician uses a voice command or hand gesture to capture an image.
285. The application 344 displays an image captured by the eyewear device 202.
286. Pharmacy technician reviews the image.
287. Pharmacy technician captures additional images (as needed).

Pharmacy technician compounds a non-hazardous IV liquid drug from a liquid MDV into an IV container in a laminar flow hood or biological safety cabinet; verification of images is required by pharmacist during preparation before a dose can be completed:

1. Pharmacy technician selects a dose in a queue from the eyewear device 202 using a voice or hand gesture command.
2. The application 344 prompts corresponding label to be printed for a final container application.
3. Pharmacy technician retrieves the label.
4. Pharmacy technician retrieves products required to complete the drug preparation.
5. The application 344 displays information to the pharmacy technician to prompt a next action.
6. Pharmacy technician uses a voice command or hand gesture to trigger scan of each barcode being used in the dose preparation.
7. Sound alerts the pharmacy technician that the scan was "captured" (not necessarily correctly).
8. The application 344 prompts the pharmacy technician whether any barcode scans were incorrect.
9. Pharmacy technician requests a next step using a voice or hand gesture command.
10. The application 344 prompts the pharmacy technician to record the LOT and expiration date of the drug.
11. Pharmacy technician records the LOT and expiration date of the drug using a voice or hand gesture command.
12. Pharmacy technician requests a next step using a voice or hand gesture command.
13. The application 344 prompts the pharmacy technician to apply a label to the final container.
14. Pharmacy technician confirms the label was applied.
15. Pharmacy technician requests a next step using a voice or hand gesture command.
16. The application 344 prompts the pharmacy technician to take a picture of the vials and solution container.
17. Pharmacy technician uses a voice command or hand gesture to capture the image.
18. The application 344 displays the image captured by the eyewear device 202.
19. Pharmacy technician reviews the image.
20. Pharmacy technician captures additional images (as needed).
21. Pharmacy technician requests a next step using a voice or hand gesture command.
22. The application 344 provides the pharmacy technician with a volume of drug to withdraw from the vial into a syringe.
23. Pharmacy technician withdraws the required volume of drug from the vial into the syringe.
24. Pharmacy technician requests a next step using a voice or hand gesture command.
25. The application 344 prompts the pharmacy technician to take a picture of the syringe.
26. Pharmacy technician uses a voice command or hand gesture to capture the image.
27. The application 344 displays the image captured by the eyewear device 202.
28. Pharmacy technician reviews the image.
29. Pharmacy technician captures additional images (as needed).
30. Pharmacy technician uses a voice command or hand gesture to capture an image.
31. Pharmacy technician requests a next step using a voice or hand gesture command.

32. The application 344 displays the image captured by the eyewear device 202.
33. Pharmacy technician reviews the image.
34. Pharmacy technician captures additional images (as needed).
35. The application 344 prompts the pharmacy technician to inject the drug from the syringe to the final container.
36. Pharmacy technician injects the required amount of drug into the final container.
37. Pharmacy technician requests a next step using a voice or hand gesture command.
38. The application 344 prompts the pharmacy technician to take a picture of a final preparation.
39. Pharmacy technician uses a voice command or hand gesture to capture the image.
40. The application 344 displays the image captured by the eyewear device 202.
41. Pharmacy technician reviews the image.
42. Pharmacy technician captures additional images (as needed).
43. Pharmacy technician requests a next step using a voice or hand gesture command.
44. The application 344 prompts the pharmacy technician to scan the final container preparation.
45. Pharmacy technician scans the final container preparation.

Pharmacy technician compounds a non-hazardous IV liquid drug from a liquid MDV into an IV container in a laminar flow hood or biological safety cabinet:

1. Pharmacy technician selects a dose in a queue from the eyewear device 202 using a voice or hand gesture command.
2. The application 344 prompts corresponding label to be printed for a final container application.
3. Pharmacy technician retrieves the label.
4. Pharmacy technician retrieves products required to complete a drug preparation.
5. The application 344 displays information to the pharmacy technician to prompt a next action.
6. Pharmacy technician uses a voice command or hand gesture to trigger a scan of each barcode being used in the dose preparation.
7. Sound alerts the pharmacy technician that the scan was "captured" (not necessarily correctly).
8. The application 344 prompts the pharmacy technician whether any barcode scans were incorrect.
9. Pharmacy technician requests a next step using a voice or hand gesture command.
10. The application 344 prompts the pharmacy technician to record the LOT and expiration date of the drug.
11. Pharmacy technician records the LOT and expiration date of the drug using a voice or hand gesture command.
12. Pharmacy technician requests a next step using a voice or hand gesture command.
13. The application 344 prompts the pharmacy technician to apply a label to the final container.
14. Pharmacy technician confirms the label was applied.
15. Pharmacy technician requests a next step using a voice or hand gesture command.
16. The application 344 prompts the pharmacy technician to take a picture of the vials and solution container.
17. Pharmacy technician uses a voice command or hand gesture to capture the image.
18. The application 344 displays the image captured by the eyewear device 202.
19. Pharmacy technician reviews the image.
20. Pharmacy technician captures additional images (as needed).
21. Pharmacy technician requests a next step using a voice or hand gesture command.
22. The application 344 provides the pharmacy technician with a volume of drug to withdraw from the vial into a syringe.
23. Pharmacy technician withdraws the required volume of drug from the vial into the syringe.
24. Pharmacy technician requests a next step using a voice or hand gesture command.
25. The application 344 prompts the pharmacy technician to take a picture of the syringe.
26. Pharmacy technician uses a voice command or hand gesture to capture the image.
27. The application 344 displays the image captured by the eyewear device 202.
28. Pharmacy technician reviews the image.
29. Pharmacy technician captures additional images (as needed).
30. Pharmacy technician uses a voice command or hand gesture to capture the image.
31. Pharmacy technician requests a next step using a voice or hand gesture command.
32. The application 344 displays the image captured by the eyewear device 202.
33. Pharmacy technician reviews the image.
34. Pharmacy technician captures additional images (as needed).
35. The application 344 prompts the pharmacy technician to inject the drug from the syringe to the final container.
36. Pharmacy technician injects the required drug from the syringe into the final container.
37. Pharmacy technician requests a next step using a voice or hand gesture command.
38. The application 344 prompts the pharmacy technician to take a picture of final preparation.
39. Pharmacy technician uses a voice command or hand gesture to capture the image.
40. The application 344 displays the image captured by the eyewear device 202.
41. Pharmacy technician reviews the image.
42. Pharmacy technician captures additional images (as needed).
43. Pharmacy technician requests a next step using a voice or hand gesture command.
44. The application 344 prompts the pharmacy technician to scan the final container preparation.
45. Pharmacy technician scans a final container preparation.

Pharmacy technician docks a non-hazardous standard dose vial into a Mini-Bag Plus container in a laminar flow hood or biological safety cabinet:

1. Pharmacy technician selects a dose in a queue from the eyewear device 202 using a voice or hand gesture command.
2. The application 344 prompts a corresponding label to be printed for a final container application.
3. Pharmacy technician retrieves the label.
4. Pharmacy technician retrieves products required to complete the drug preparation.
5. The application 344 displays information to the pharmacy technician to prompt a next action.
6. Pharmacy technician uses a voice command or hand gesture to trigger a scan of each barcode being used in the dose preparation.

7. Sound alerts the pharmacy technician that the scan was "captured" (not necessarily correctly).
8. The application 344 prompts the pharmacy technician whether any barcode scans were incorrect.
9. Pharmacy technician requests a next step using a voice or hand gesture command.
10. The application 344 prompts the pharmacy technician to record the LOT and expiration date of the drug.
11. Pharmacy technician records the LOT and expiration date of the drug using a voice or hand gesture command.
12. Pharmacy technician requests a next step using a voice or hand gesture command.
13. The application 344 prompts the pharmacy technician to take a picture of the vial and a Mini-Bag Plus container.
14. Pharmacy technician uses a voice command or hand gesture to capture the image.
15. The application 344 displays the image captured by the eyewear device 202.
16. Pharmacy technician reviews the image.
17. Pharmacy technician captures additional images (as needed).
18. Pharmacy technician requests a next step using a voice or hand gesture command.
19. The application 344 prompts the pharmacy technician to dock vial to the Mini-Bag Plus container.
20. Pharmacy technician requests a next step using a voice or hand gesture command.
21. The application 344 prompts the pharmacy technician to take a picture of the docked vial and the Mini-Bag Plus container.
22. Pharmacy technician uses a voice command or hand gesture to capture the image.
23. The application 344 displays the image captured by the eyewear device 202.
24. Pharmacy technician reviews the image.
25. Pharmacy technician captures additional images (as needed).
26. Pharmacy technician requests a next step using a voice or hand gesture command.
27. The application 344 prompts the pharmacy technician to apply a label to the final container.
28. Pharmacy technician confirms the label was applied.
29. Pharmacy technician requests a next step using a voice or hand gesture command.
30. The application 344 prompts the pharmacy technician to scan the final container preparation.
31. Pharmacy technician scans the final container preparation.

Pharmacy technician prepares an oral solid dose in a laminar flow hood or biological safety cabinet 1. Pharmacy technician selects a dose in a queue from the eyewear device 202 using a voice or hand gesture command.
2. The application 344 prompts a corresponding label to be printed for a final container application.
3. Pharmacy technician retrieves the label.
4. Pharmacy technician retrieves product(s) required to complete the drug preparation.
5. The application 344 displays information to the pharmacy technician to prompt a next action.
6. Pharmacy technician uses a voice command or hand gesture to trigger a scan of a source container(s) or a WIP label on the source container(s) for the oral doses.
7. Sound alerts the pharmacy technician that the scan was "captured" (not necessarily correctly).
8. The application 344 prompts the pharmacy technician whether any barcode scans were incorrect.
9. Pharmacy technician requests a next step using a voice or hand gesture command.
10. The application 344 prompts the pharmacy technician to record the LOT and expiration date of the drug.
11. Pharmacy technician records the LOT and expiration date of the drug using a voice or hand gesture command.
12. Pharmacy technician requests a next step using a voice or hand gesture command.
13. System prompts the pharmacy technician to enter a quantity tablets required for the dose.
14. Pharmacy technician selects the total quantity tablets required for the dose via the eyewear device 202 using a voice or hand gesture command.
15. Pharmacy technician requests a next step using a voice or hand gesture commend.
16. The application 344 prompts the pharmacy technician to scan the container that the oral dose will be transferred.
17. Pharmacy technician scans the final container that the oral dose will be transferred.
18. Sound alerts the pharmacy technician that the scan was "captured" (not necessarily correctly).
19. The application 344 prompts the pharmacy technician whether any barcode scans were incorrect.
20. Pharmacy technician requests a next step using a voice or hand gesture command.
21. The application 344 displays a quantity of oral tablets to be prepared.
22. Pharmacy technician removes the appropriate quantity of oral tablets from the source container(s).
23. Pharmacy technician requests a next step using a voice or hand gesture command.
24. The application 344 prompts the pharmacy technician to take a photo of a source container(s) and tablets.
25. Pharmacy technician uses a voice command or hand gesture to capture the image.
26. The application 344 displays the image captured by the eyewear device 202.
27. Pharmacy technician reviews the image.
28. Pharmacy technician captures additional images (as needed).
29. Pharmacy technician requests a next step using a voice or hand gesture command.
30. The application 344 prompts the pharmacy technician to transfer the tablets into final container(s).
31. Pharmacy technician transfers the required quantity of tablets into the final container(s).
32. Pharmacy technician requests a next step using a voice or hand gesture command.
33. The application 344 prompts the pharmacy technician to take a picture of final container(s).
34. Pharmacy technician uses a voice command or hand gesture to capture the image.
35. The application 344 displays the image captured by the eyewear device 202.
36. Pharmacy technician reviews the image.
37. Pharmacy technician captures additional images (as needed).
38. Pharmacy technician requests a next step using a voice or hand gesture command.
39. The application 344 prompts the pharmacy technician to scan the final container(s) preparation.
40. Pharmacy technician scans the final container(s) preparation.

Pharmacy technician prepares pre-mix drug in a laminar flow hood or biological safety cabinet:
1. Pharmacy technician selects a dose in a queue from the eyewear device 202 using a voice or hand gesture command.
2. The application 344 prompts a corresponding label to be printed for a final container application.
3. Pharmacy technician retrieves the label.
4. Pharmacy technician retrieves products required to complete the drug preparation.
5. The application 344 displays information to the pharmacy technician to prompt a next action.
6. Pharmacy technician uses a voice command or hand gesture to trigger a scan of each barcode being used in the dose preparation.
7. Sound alerts the pharmacy technician that the scan was "captured" (not necessarily correctly).
8. The application 344 prompts the pharmacy technician whether any barcode scans were incorrect.
9. Pharmacy technician requests a next step using a voice or hand gesture command.
10. The application 344 prompts the pharmacy technician to record the LOT and expiration date of the drug.
11. Pharmacy technician records the LOT and expiration date of the drug using a voice or hand gesture command.
12. Pharmacy technician requests a next step using a voice or hand gesture command.
13. The application 344 prompts the pharmacy technician to take a picture of a premix drug container.
14. Pharmacy technician uses a voice command or hand gesture to capture the image.
15. The application 344 displays the image captured by the eyewear device 202.
16. Pharmacy technician reviews the image.
17. Pharmacy technician captures additional images (as needed).
18. Pharmacy technician requests a next step using a voice or hand gesture command.
19. The application 344 prompts the pharmacy technician to apply a label to the final container.
20. Pharmacy technician confirms the label was applied.
21. Pharmacy technician requests a next step using a voice or hand gesture command.
22. Pharmacy technician captures additional images (as needed).
23. Pharmacy technician requests a next step using a voice or hand gesture command.
24. The application 344 prompts the pharmacy technician to scan the final premix container preparation.
25. Pharmacy technician scans the final premix container preparation.

Pharmacy technician compounds a non-hazardous IV liquid drug from a liquid MDV into an IV container in a laminar flow hood or biological safety cabinet. Verification of images is required by pharmacist during preparation before dose can be completed:
1. Pharmacy technician selects a dose in a queue from the eyewear device 202 using a voice or hand gesture command.
2. System prompts a corresponding label to be printed for a final container application.
3. Pharmacy technician retrieves the label.
4. Pharmacy technician retrieves products required to complete drug preparation.
5. The application 344 displays information to the pharmacy technician to prompt a next action.
6. Pharmacy technician uses a voice command or hand gesture to trigger a scan of each barcode being used in the dose preparation.
7. Sound alerts the pharmacy technician that the scan was "captured" (not necessarily correctly).
8. The application 344 prompts the pharmacy technician whether any barcode scans were incorrect.
9. Pharmacy technician requests a next step using a voice or hand gesture command.
10. The application 344 prompts the pharmacy technician to record the LOT and expiration date of the drug.
11. Pharmacy technician records the LOT and expiration date of the drug using a voice or hand gesture command.
12. Pharmacy technician requests a next step using a voice or hand gesture command.
13. The application 344 prompts the pharmacy technician to apply a label to the final container.
14. Pharmacy technician confirms the label was applied.
15. Pharmacy technician requests a next step using a voice or hand gesture command.
16. The application 344 prompts the pharmacy technician to take a picture of the vials and solution container.
17. Pharmacy technician uses a voice command or hand gesture to capture the image.
18. The application 344 displays the image captured by the eyewear device 202.
19. Pharmacy technician reviews the image.
20. Pharmacy technician captures additional images (as needed).
21. Pharmacy technician requests a next step using a voice or hand gesture command.
22. The application 344 prompts the pharmacy technician with a volume of a drug to withdraw from the vial into a syringe.
23. Pharmacy technician withdraws the required volume of the drug from vial into the syringe.
24. Pharmacy technician requests a next step using a voice or hand gesture command.
25. The application 344 prompts the pharmacy technician to take a picture of the syringe.
26. Pharmacy technician uses a voice command or hand gesture to capture the image.
27. The application 344 displays the image captured by the eyewear device 202.
28. Pharmacy technician reviews the image.
29. Pharmacy technician captures additional images (as needed).
30. Pharmacy technician uses a voice command or hand gesture to capture the image.
31. Pharmacy technician requests a next step using a voice or hand gesture command.
32. The application 344 displays the image captured by the eyewear device 202.
33. Pharmacy technician reviews the image.
34. Pharmacy technician captures additional images (as needed).
35. Pharmacy technician waits for in-line verification to be completed.
36. The application 344 returns pharmacy technician to the dose queue.
37. Pharmacy technician waits for in-line verification to be completed by a pharmacist.
38. System notifies that review is complete by dose being displayed in the resume prep queue.

39. Pharmacy technician selects this dose from the resume prep queue from the eyewear device 202 using a voice or hand gesture commend.
40. The application 344 prompts the pharmacy technician to scan a label of the in-line dose.
41. Pharmacy technician scans the dose label to resume drug preparation.
42. The application 344 prompts the pharmacy technician to inject a drug from a syringe to a final container.
43. Pharmacy technician injects the required amount of the drug into the final container.
44. Pharmacy technician requests a next step using a voice or hand gesture command.
45. The application 344 prompts the pharmacy technician to take a picture of final preparation.
46. Pharmacy technician uses a voice command or hand gesture to capture the image.
47. The application 344 displays the image captured by the eyewear device 202.
48. Pharmacy technician reviews the image.
49. Pharmacy technician captures additional images (as needed).
50. Pharmacy technician requests a next step using a voice or hand gesture command.
51. The application 344 prompts the pharmacy technician to scan the final container preparation.
52. Pharmacy technician scans the final container preparation.

Pharmacy technician reconstitutes and admixes a solid or lyophilized non-hazardous drug into a flexible IV container in a laminar flow hood or biological safety cabinet:

1. Pharmacy technician selects a dose in a queue from the eyewear device 202 using a voice or hand gesture command.
2. System prompts a corresponding label to be printed for a final container application.
3. Pharmacy technician retrieves the label.
4. Pharmacy technician retrieves products required to complete the drug preparation.
5. The application 344 displays information to the pharmacy technician to prompt a next action.
6. Pharmacy technician uses a voice command or hand gesture to trigger a scan of each vial(s) required for drug reconstitution.
7. Sound alerts the pharmacy technician that the scan was "captured" (not necessarily correctly).
8. The application 344 prompts the pharmacy technician whether any barcode scans were incorrect.
9. Pharmacy technician requests a next step using a voice or hand gesture command.
10. The application 344 prompts the pharmacy technician to record the LOT and expiration date of the drug.
11. Pharmacy technician records the LOT and expiration date of the drug using a voice or hand gesture command.
12. Pharmacy technician requests a next step using a voice or hand gesture command.
13. The application 344 prompts the pharmacy technician to scan a diluent required for the drug reconstitution.
14. Pharmacy technician uses a voice command or hand gesture to trigger a scan of diluent(s) required for the drug reconstitution.
15. Pharmacy technician requests a next steps using a voice or hand gesture command.
16. The application 344 prompts the pharmacy technician to record the LOT and expiration date of the drug.
17. Pharmacy technician records the LOT and expiration date of the drug using a voice or hand gesture command.
18. Pharmacy technician requests a next step using a voice or hand gesture command.
19. The application 344 displays a volume of diluent required for the dose.
20. Pharmacy technician withdraws the appropriate volume of diluent required into the syringe.
21. Pharmacy technician requests a next step using a voice or hand gesture command.
22. The application 344 prompts the pharmacy technician to take a picture of the diluent withdrawn into the syringe.
23. Pharmacy technician uses a voice command or hand gesture to capture the image.
24. The application 344 displays the image captured by the eyewear device 202.
25. Pharmacy technician reviews the image.
26. Pharmacy technician captures additional images (as needed).
27. Pharmacy technician requests a next step using a voice or hand gesture command.
28. The application 344 prompts the pharmacy technician to reconstitute the drug product by inserting a diluent into the drug vial.
29. Pharmacy technician inserts the diluent into the drug vial.
30. Pharmacy technician requests a next step using a voice or hand gesture command.
31. The application 344 prompts the pharmacy technician to take a picture of the final reconstituted vial.
32. Pharmacy technician uses a voice command or hand gesture to capture the image.
33. The application 344 displays the image captured by the eyewear device 202.
34. Pharmacy technician reviews the image.
35. Pharmacy technician captures additional images (as needed).
36. Pharmacy technician requests a next step using a voice or hand gesture command.
37. The application 344 prompts the pharmacy technician to gather or prepare any additional ingredients required for the final container.
38. Pharmacy technician gathers or prepares any additional ingredients required for the final container.
39. Pharmacy technician requests a next step using a voice or hand gesture command.
40. The application 344 prompts the pharmacy technician to complete any additional steps required for final container preparation.
41. Pharmacy technician completes any additional steps required for final container preparation.
42. Pharmacy technician requests a next step using a voice or hand gesture command.
43. The application 344 prompts the pharmacy technician to inject a final dose into the drug container
44. Pharmacy technician injects the final dose into the drug container.
45. Pharmacy technician requests a next step using a voice or hand gesture command.
46. The application 344 prompts the pharmacy technician to apply a label to the final container.
47. Pharmacy technician confirms the label was applied.
48. Pharmacy technician requests a next step using a voice or hand gesture command.

49. The application 344 prompts the pharmacy technician to take a picture of final preparation.
50. Pharmacy technician uses a voice command or hand gesture to capture the image.
51. The application 344 displays the image captured by the eyewear device 202.
52. Pharmacy technician reviews the image.
53. Pharmacy technician captures additional images (as needed).
54. Pharmacy technician requests a next step using a voice or hand gesture command.
55. The application 344 prompts the pharmacy technician to scan the final container preparation.
56. Pharmacy technician scans the final container preparation.

Pharmacy technician reconstitutes and admixes a solid or lyophilized non-hazardous drug into a syringe final container in a laminar flow hood or biological safety cabinet:

1. Pharmacy technician selects a dose in a queue from the eyewear device 202 using a voice or hand gesture command.
2. System requests a corresponding label to be printed for a final container application.
3. Pharmacy technician retrieves the label.
4. Pharmacy technician retrieves products required to complete the drug preparation.
5. The application 344 displays information to the pharmacy technician to prompt a next action.
6. Pharmacy technician uses a voice command or hand gesture to trigger a scan of each vial(s) required for drug reconstitution.
7. Sound alerts the pharmacy technician that the scan was "captured" (not necessarily correctly).
8. The application 344 prompts the pharmacy technician whether any barcode scans were incorrect.
9. Pharmacy technician requests a next step using a voice or hand gesture command.
10. The application 344 prompts the pharmacy technician to record the LOT and expiration date of the drug.
11. Pharmacy technician records the LOT and expiration date of the drug using a voice or hand gesture command.
12. Pharmacy technician requests a next step using a voice or hand gesture command.
13. The application 344 prompts the pharmacy technician to scan the diluent required for drug reconstitution.
14. Pharmacy technician uses a voice command or hand gesture to trigger a scan of diluent(s) required for drug reconstitution.
15. Pharmacy technician requests a next steps using a voice or hand gesture command.
16. The application 344 prompts the pharmacy technician to record the LOT and expiration date of the drug.
17. Pharmacy technician records the LOT and expiration date of the drug using a voice or hand gesture command.
18. Pharmacy technician requests a next step using a voice or hand gesture command.
19. The application 344 displays a volume of diluent required for the dose.
20. Pharmacy technician withdraws the appropriate volume of diluent required into syringe.
21. Pharmacy technician requests a next step using a voice or hand gesture command.
22. The application 344 prompts the pharmacy technician to take a picture of the diluent withdrawn into the syringe.
23. Pharmacy technician uses a voice command or hand gesture to capture the image.
24. The application 344 displays the image captured by the eyewear device 202.
25. Pharmacy technician reviews the image.
26. Pharmacy technician captures additional images (as needed).
27. Pharmacy technician requests a next step using a voice or hand gesture command.
28. The application 344 prompts the pharmacy technician to reconstitute the drug product by inserting the diluent into the drug vial.
29. Pharmacy technician inserts a diluent into the drug vial.
30. Pharmacy technician requests a next step using a voice or hand gesture command.
31. The application 344 prompts the pharmacy technician to take a picture of the final reconstituted vial.
32. Pharmacy technician uses a voice command or hand gesture to capture the image.
33. The application 344 displays the image captured by the eyewear device 202.
34. Pharmacy technician reviews the image.
35. Pharmacy technician captures additional images (as needed).
36. Pharmacy technician requests a next step using a voice or hand gesture command.
37. The application 344 prompts the pharmacy technician to gather or prepare any additional ingredients required for the final container.
38. Pharmacy technician gathers or prepares any additional ingredients required for the final container.
39. Pharmacy technician requests a next step using a voice or hand gesture command.
40. The application 344 prompts the pharmacy technician to complete any additional steps required for final container preparation.
41. Pharmacy technician completes any additional steps required for final syringe preparation.
42. Pharmacy technician requests a next step using a voice or hand gesture command.
43. The application 344 prompts the pharmacy technician to withdraw a final dose into the syringe.
44. Pharmacy technician withdraws the final dose into the syringe.
45. Pharmacy technician requests a next step using a voice or hand gesture command.
46. The application 344 prompts the pharmacy technician to apply a label to the final container.
47. Pharmacy technician confirms the label was applied.
48. Pharmacy technician requests a next step using a voice or hand gesture command.
49. The application 344 prompts the pharmacy technician to take a picture of a final syringe preparation.
50. Pharmacy technician uses a voice command or hand gesture to capture the image.
51. The application 344 displays the image captured by the eyewear device 202.
52. Pharmacy technician reviews the image.
53. Pharmacy technician captures additional images (as needed).
54. Pharmacy technician requests a next step using a voice or hand gesture command.
55. The application 344 prompts the pharmacy technician to scan the final syringe preparation.
56. Pharmacy technician scans a final syringe preparation.

Conclusion

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A heads-up display ("HUD") system comprising:
an eyewear device including:
 a frame including a right lens, a left lens, a bridge connecting the right lens and the left lens, a first arm connected to the right lens, and a second arm connected to the left lens,
 a camera connected to or integrated with the frame,
 a microphone and speaker connected to or integrated with the first arm or the second arm, and
 a display module including a screen that is positioned in front of or behind the right lens or the left lens with respect to a viewpoint of a wearer; and
a client device communicatively coupled to the eyewear device, the client device including a processor and a memory device storing instructions defining an application, execution of the instructions causing the processor of the client device to:
 cause the application to communicatively couple to a pharmacy server storing a plurality of dose orders for medication doses ordered for preparation,
 cause the display module of the eyewear device to display a user interface that includes at least a portion of the plurality of dose orders,
 receive an input via the microphone or the camera indicative of a dose order for selection,
 receive a dose order file from the pharmacy server, the dose order file corresponding to the selected dose order,
 receive or retrieve a preparation protocol based on a medication type of the dose order file, the preparation protocol including a sequence of steps for preparing a medication dose for the selected dose order, each step in the sequence of steps associated with graphical step instructions for the wearer, at least one of the steps of the sequence of steps requiring a digital image to be recorded,
 for each step of the preparation protocol, display corresponding graphical step instructions on the screen of the eyewear device,
 when a step of the preparation protocol requires the recording of a digital image, activate the camera for recording the digital image,
 when a step of the preparation protocol requires user entry of verification information, (i) display, in conjunction with graphical step instructions of the step, options for voice entry via the microphone or digital image entry via the camera, and (ii) progress to a next step of the preparation protocol after the verification information is received, and
 store to a verification file, an indication of completion progress of the preparation protocol, recorded digital images, and the verification information.

2. The system of claim 1, wherein the graphical step instructions for each step are displayed adjacent to a graphical indication of required ingredients that specifies a quantity of each ingredient needed and a quantity of each ingredient already obtained.

3. The system of claim 1, wherein the application is configured to authenticate the wearer with the pharmacy server before having access to the plurality of dose orders.

4. The system of claim 3, wherein the plurality of dose orders is selected by the pharmacy server among all received dose orders based on the authentication of the wearer.

5. The system of claim 1, wherein the at least one step of the sequence of steps requires the recording of the digital image of at least one of:
 a label or a barcode of an ingredient container;
 a preparation container;
 a display of a weight scale or balance; or
 an administration container.

6. The system of claim 1, wherein the camera is a first camera module that is located on the bridge, the eyewear device including a second camera module located on the first arm or the second arm.

7. The system of claim 6, wherein the first camera module includes a high-resolution camera with at least five megapixels and the second camera module includes an optical zoom, a barcode scanner, and a laser pointer.

8. The system of claim 6, wherein a touchpad is included with the second camera module or a housing of the microphone and speaker.

9. The system of claim 6, wherein the processor of the client device in conjunction with the second camera module causes the second camera module to zoom and crop a digital image around a detected label or a barcode.

10. The system of claim 1, wherein the graphical step instructions are first graphical step instructions for display at the eyewear device, the preparation protocol including second graphical step instructions that are configured for display on the client device, the second graphical step instructions including additional preparation content that is omitted from the first graphical step instructions.

11. The system of claim 1, wherein the processor is further configured to:
 receive, from the microphone of the eyewear device, an audio signal;
 convert the audio signal into text;
 determine the text corresponds to a voice command to start a video call with a pharmacist;
 use a video conference feature of the client device to connect to a device of the pharmacist; and
 activate the camera to transmit recorded video to the device of the pharmacist during a video conference with the pharmacist.

12. A heads-up display ("HUD") system comprising:
an eyewear device including:
 a frame including a right lens, a left lens, a bridge connecting the right lens and the left lens, a first arm connected to the right lens, and a second arm connected to the left lens,
 a barcode scanner connected to or integrated with the frame,
 a microphone and speaker connected to or integrated with the first arm or the second arm, and
 a display module including a screen that is positioned in front of or behind the right lens or the left lens with respect to a viewpoint of a wearer; and
a client device communicatively coupled to the eyewear device, the client device including a processor and a memory device storing instructions defining an application, execution of the instructions causing the processor of the client device to:

cause the application to communicatively couple to a pharmacy server storing a plurality of dose orders for medication doses ordered for preparation, cause the display module of the eyewear device to display a user interface that includes at least a portion of the plurality of dose orders, receive an input via the microphone indicative of a dose order for selection, receive a dose order file from the pharmacy server, the dose order file corresponding to the selected dose order, receive or retrieve a preparation protocol based on a medication type of the dose order file, the preparation protocol including a sequence of steps for preparing a medication dose for the selected dose order, each step in the sequence of steps associated with graphical step instructions for the wearer, at least one of the steps of the sequence of steps requiring a barcode of an ingredient container to be scanned, for each step of the preparation protocol, display corresponding graphical step instructions on the screen of the eyewear device, when a step of the preparation protocol requires the scanning of a barcode, activate the barcode scanner, when a step of the preparation protocol requires user entry of verification information, (i) display, in conjunction with graphical step instructions of the step, a text box for voice entry via the microphone, and (ii) progress to a next step of the preparation protocol after the verification information is received, and store to a verification file, an indication of completion progress of the preparation protocol, data from scanned barcodes, and the verification information.

13. The system of claim 12, wherein when the step of the preparation protocol requires user entry of the verification information, the processor is configured to display, in conjunction with a user interface of the step, options for voice entry via the microphone or barcode scanning using the barcode scanner.

14. The system of claim 12, wherein the processor is further configured to:

Compare the verification information to verification limits specified in the preparation protocol;

when at least some of the verification information is outside of the respective verification limits, cause an error message to be displayed by the display screen of the eyewear device; and when the verification information is within the respective verification limits, store the verification information to the verification file.

15. The system of claim 14, wherein the comparison to the verification limits is performed during each step, and wherein the processor is configured to prevent graphical step instructions for a next step from being displayed at the display screen of the eyewear device until the verification information is within the respective verification limits.

16. The system of claim 12, wherein the processor is further configured to:

receive, from the microphone of the eyewear device, an audio signal;

convert the audio signal into text;

determine the text corresponds to a voice command to call a pharmacist; and use a call feature of the client device to connect to a device of the pharmacist.

17. The system of claim 12, wherein the eyewear device further includes at least one camera module having a camera to record at least one of digital images or video for at least some of the verification information.

18. The system of claim 12, wherein the processor is further configured to update the preparation protocol with at least some information from the dose order file.

19. The system of claim 12, wherein the processor is further configured to transmit the verification file to the pharmacy server after the preparation protocol is complete.

20. The system of claim 19, wherein the processor is further configured to:

receive, from the pharmacy server, a message indicative that at least some of the verification information of the verification file is not correct; and cause the display module of the eyewear device to display a notification indicative of the message.

* * * * *